United States Patent
D'Alessio et al.

(10) Patent No.: US 7,585,952 B2
(45) Date of Patent: Sep. 8, 2009

(54) HUMAN MINI-ANTIBODY CYTOTOXIC FOR TUMOR CELLS WHICH EXPRESS THE ERBB2 RECEPTOR

(75) Inventors: Giuseppe D'Alessio, Naples (IT); Renata Piccoli, Naples (IT); Claudia De Lorenzo, Naples (IT); Donald Balfour Palmer, Wembley, Middelsex (GB); Mary Alice Ritter, London (GB)

(73) Assignee: Biotechnol S.A., Oeiras (PT)

( * ) Notice: Subject to any disclaimer, the term of this patent is extended or adjusted under 35 U.S.C. 154(b) by 857 days.

(21) Appl. No.: 10/483,803

(22) PCT Filed: Jul. 10, 2002

(86) PCT No.: PCT/EP02/07671

§ 371 (c)(1),
(2), (4) Date: Jan. 12, 2004

(87) PCT Pub. No.: WO03/006509

PCT Pub. Date: Jan. 23, 2003

(65) Prior Publication Data

US 2007/0258985 A1 Nov. 8, 2007

(30) Foreign Application Priority Data

Jul. 10, 2001 (IT) .......................... RM2001A0408

(51) Int. Cl.
| C12P 21/08 | (2006.01) |
| A61K 39/395 | (2006.01) |
| A61K 39/00 | (2006.01) |
| C12P 21/04 | (2006.01) |

(52) U.S. Cl. .............. 530/387.3; 424/130.1; 424/178.1; 435/69.6

(58) Field of Classification Search ........................ None
See application file for complete search history.

(56) References Cited

U.S. PATENT DOCUMENTS

| 6,135,941 A | 10/2000 | Hillman et al. |
| 7,244,826 B1 | 7/2007 | Marks et al. |

FOREIGN PATENT DOCUMENTS

| JP | 07 309780 | 11/1995 |
| WO | WO 96/25436 | 8/1996 |
| WO | WO 99/47685 | 9/1999 |
| WO | WO 99/56129 | 11/1999 |
| WO | WO 99/57266 | 11/1999 |
| WO | WO 01/14558 | 3/2001 |
| WO | WO 01/27279 | 4/2001 |

OTHER PUBLICATIONS

Skolnick et al. Trends in Biotechnology, 18(1):34-39, 2000.*
Burgess et al, Journal of Cell Biology vol. 111 Nov. 1990 2129-2138.*
Lazar et al Molecular and Cellular Biology Mar. 1988 vol. 8 No. 3 1247-1252.*
Paul, Fundamental Immunology, 3rd Edition, 1993, pp. 292-295.*
Rudikoff et al. Proc. Natl. Acad. Sci. USA, 79:1979-1983, Mar. 1982.*
Colman. Research in Immunology, 145:33-36, 1994.*
Bendig M. M. Methods: A Companion to Methods in Enzymology, 1995; 8:83-93.*
MacCallum et al. J. Mol. Biol., 262, 732-745, 1996.*
Casset et al. Biochemical and Biophysical Research Communications, 307:198-205, 2003.*
Schier et al., Immunotechnology, 1995, 1:73-81.*
De Lorenzo et al., "A New Human Antitumor Immunoreagent Specific for ErbB2[1]," *Clinical Cancer Research* (2002) 8:1710-1719.
Griffiths et al., "Isolation of high affinity human antibodies directly from large synthetic repertoires," *EMBO J* (1994) 13(14):3245-3260.
Hoogenboom et al., "Antibody phage display technology and its applications," *Immunotechnology* (1998) 4(1):1-20.
Hoogenboom et al., "Designing and optimizing library selection strategies for generating high-affinity antibodies," *Trends Biotechnol.* (1997) 15(2):62-70.
Kawasaki et al., "BAA20902," NCBI, 'Online!', Nov. 6, 1999; retrieved from the internet: <URL:http://www.ncbi.nlm.gov/entrez/viewer.fcgi?val=BAA20902.1>.
Müller et al., "The first constant domain ($C_H1$ and $C_L$) of an antibody used as heterodimerization domain for bispecific miniantibodies," *FEBS Letters* (1998) 422:259-264.
Perera et al., "V(D)J germline gene repertoire analysis of monoclonal D antibodies and the implications for D epitope specificity," *Transfusion* (2000) 40:846-855.
Poul et al., "Selection of Tumor-Specific Internalizing Human Antibodies from Phage Libraries," *J. Mol. Biol.* (2000) 301:1149-1161.
Sarup et al., "Characterization of an Anti-p185$^{HER\ 2}$ Monoclonal Antibody that Stimulates Receptor Function and Inhibits Tumor Cell Growth," *Growth Regulation* (1991) 1(2):72-82.
Wels et al., "EGF Receptor and p185$^{erB-2}$-Specific Single-Chain Antibody Toxins Differ in Their Cell-Killing Activity on Tumor Cells Expressing Both Receptor Proteins," *Int J Canc* (1995) 60(1):137-144.
Zewe et al., "Cloning and cytotoxicity of a human pancreatic RNase immunofusion," *Immunotechnology* (1997) 3:127-136.

* cited by examiner

Primary Examiner—Christopher H Yaen
Assistant Examiner—Hong Sang
(74) *Attorney, Agent, or Firm*—Joseph R. Baker, Jr.; Gavrilovich Dodd & Lindsey LLP

(57) ABSTRACT

The invention refers to a fully human miniantibody (scFv), called Erbicin, specific for the receptor ErbB2, with a pharmacological, in particular antitumour, activity. It has been obtained from a larger fagmidic library (Griffin 1.) (19) of human synthetic scFv by panning (affinity selection on antigen) carried out on live cells that express various levels of ErbB2. The invention relates also to the DNA and aniino acid sequences of said antibody, to the procedure for isolating it, to its use in therapy.

44 Claims, 8 Drawing Sheets

A

B

SEQUENCE LISTING

<160> NUMBER OF SEQ ID NOS: 24

<210> SEQ ID NO 1
<211> LENGTH: 339
<212> TYPE: DNA
<213> ORGANISM: Homo sapiens

<400> SEQUENCE: 1

```
caggtgcagc tgttgcagtc tgcagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca agtccatcag caccgcctac     240
ctgcagtgga gcagcctgaa ggcctcggac acggccgtgt attactgtgc aagatggcgt     300
gattcgcctt tgtggggcca aggtaccctg gtcaccgtc                            339
```

<210> SEQ ID NO 2
<211> LENGTH: 113
<212> TYPE: PRT
<213> ORGANISM: Homo sapiens

<400> SEQUENCE: 2

Gln Val Gln Leu Leu Gln Ser Ala Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Trp Arg Asp Ser Pro Leu Trp Gly Gln Gly Thr Leu Val Thr
            100                 105                 110

Val

<210> SEQ ID NO 3
<211> LENGTH: 15

```
<212> TYPE: DNA
<213> ORGANISM: Homo sapiens

<400> SEQUENCE: 3
agctactgga tcggc                                                      15

<210> SEQ ID NO 4
<211> LENGTH: 5
<212> TYPE: PRT
<213> ORGANISM: Homo sapiens

<400> SEQUENCE: 4

Ser Tyr Trp Ile Gly
1               5

<210> SEQ ID NO 5
<211> LENGTH: 51
<212> TYPE: DNA
<213> ORGANISM: Homo sapiens

<400> SEQUENCE: 5
atcatctatc ctggtgactc tgataccaga tacagcccgt ccttccaagg c              51

<210> SEQ ID NO 6
<211> LENGTH: 17
<212> TYPE: PRT
<213> ORGANISM: Homo sapiens

<400> SEQUENCE: 6

Ile Ile Tyr Pro Gly Asp Ser Asp Thr Arg Tyr Ser Pro Ser Phe Gln
1               5                   10                  15

Gly

<210> SEQ ID NO 7
<211> LENGTH: 18
<212> TYPE: DNA
<213> ORGANISM: Homo sapiens

<400> SEQUENCE: 7
tggcgtgatt cgcctttg                                                   18

<210> SEQ ID NO 8
<211> LENGTH: 6
<212> TYPE: PRT
<213> ORGANISM: Homo sapiens

<400> SEQUENCE: 8

Trp Arg Asp Ser Pro Leu
1               5

<210> SEQ ID NO 9
<211> LENGTH: 51
<212> TYPE: DNA
<213> ORGANISM: Homo sapiens

<400> SEQUENCE: 9
tcgagtggtg gaggcggttc aggcggaggt ggctctggcg gtagtgcact t              51

<210> SEQ ID NO 10
<211> LENGTH: 17
<212> TYPE: PRT
<213> ORGANISM: Homo sapiens

<400> SEQUENCE: 10
```

-continued

Ser Ser Gly Gly Gly Gly Ser Gly Gly Gly Ser Gly Gly Ser Ala
1               5                   10                  15

Leu

<210> SEQ ID NO 11
<211> LENGTH: 333
<212> TYPE: DNA
<213> ORGANISM: Homo sapiens

<400> SEQUENCE: 11
caggctgtgg tgactcagga gccatcgttc tcagtgtccc ctggagggac agtcacactc     60
acttgtggct tgagctctgg ctcagtctct actagttact accccagctg gtaccagcag    120
accccaggcc aggctccacg cacgctcatc tacagcacaa acactcgctc ttctggggtc    180
cctgatcgct tctctggctc catccttggg aacaaagctg ccctcaccat cacgggggcc    240
caggcagatg atgaatctga ttattactgt gtgctgtata tgggtagtgg ccagtatgta    300
ttcggcggag ggaccaagct gaccgtccta ggt                                 333

<210> SEQ ID NO 12
<211> LENGTH: 111
<212> TYPE: PRT
<213> ORGANISM: Homo sapiens

<400> SEQUENCE: 12

Gln Ala Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

Tyr Tyr Pro Ser Trp Tyr Gln Gln Thr Pro Gly Gln Ala Pro Arg Thr
            35                  40                  45

Leu Ile Tyr Ser Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Gln Tyr Val Phe Gly Gly Gly Thr Lys Leu Thr Val Leu Gly
            100                 105                 110

<210> SEQ ID NO 13
<211> LENGTH: 41
<212> TYPE: DNA
<213> ORGANISM: Homo sapiens

<400> SEQUENCE: 13
ggcttgagct ctggctcagt ctctactagt tactacccca g                         41

<210> SEQ ID NO 14
<211> LENGTH: 14
<212> TYPE: PRT
<213> ORGANISM: Homo sapiens

<400> SEQUENCE: 14

Gly Leu Ser Ser Gly Ser Val Ser Thr Ser Tyr Tyr Pro Ser
1               5                   10

<210> SEQ ID NO 15
<211> LENGTH: 21

```
<212> TYPE: DNA
<213> ORGANISM: Homo sapiens

<400> SEQUENCE: 15
agcacaaaca ctcgctcttc t                                              21

<210> SEQ ID NO 16
<211> LENGTH: 7
<212> TYPE: PRT
<213> ORGANISM: Homo sapiens

<400> SEQUENCE: 16

Ser Thr Asn Thr Arg Ser Ser
1               5

<210> SEQ ID NO 17
<211> LENGTH: 30
<212> TYPE: DNA
<213> ORGANISM: Homo sapiens

<400> SEQUENCE: 17
gtgctgtata tgggtagtgg ccagtatgta                                     30

<210> SEQ ID NO 18
<211> LENGTH: 10
<212> TYPE: PRT
<213> ORGANISM: Homo sapiens

<400> SEQUENCE: 18

Val Leu Tyr Met Gly Ser Gly Gln Tyr Val
1               5                   10

<210> SEQ ID NO 19
<211> LENGTH: 723
<212> TYPE: DNA
<213> ORGANISM: Homo sapiens

<400> SEQUENCE: 19
caggtgcagc tgttgcagtc tgcagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac      240 ctgcagtgga gcagcctgaa ggcctcggac acggccgtgt attactgtgc aagatggcgt     300
gattcgcctt tgtggggcca aggtaccctg gtcaccgtct cgagtggtgg aggcggttca     360
ggcggaggtg gctctggcgg tagtgcactt caggctgtgg tgactcagga gccatcgttc     420
tcagtgtccc ctggagggac agtcacactc acttgtggct tgagctctgg ctcagtctct     480
actagttact accccagctg gtaccagcag ccccaggcc aggctccacg cacgctcatc       540
tacagcacaa acactcgctc ttctggggtc cctgatcgct tctctggctc catccttggg     600
aacaaagctg ccctcaccat cacgggggcc caggcagatg atgaatctga ttattactgt     660
gtgctgtata tgggtagtgg ccagtatgta ttcggcggag ggaccaagct gaccgtccta     720
ggt                                                                  723

<210> SEQ ID NO 20
<211> LENGTH: 241
<212> TYPE: PRT
<213> ORGANISM: Homo sapiens
```

<400> SEQUENCE: 20

```
Gln Val Gln Leu Leu Gln Ser Ala Ala Glu Val Lys Lys Pro Gly Glu
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Val Tyr Tyr Cys
                85                  90                  95
Ala Arg Trp Arg Asp Ser Pro Leu Trp Gly Gln Gly Thr Leu Val Thr
            100                 105                 110
Val Ser Ser Gly Gly Gly Gly Ser Gly Gly Gly Gly Ser Gly Gly Ser
        115                 120                 125
Ala Leu Gln Ala Val Val Thr Gln Glu Pro Ser Phe Ser Val Ser Pro
    130                 135                 140
Gly Gly Thr Val Thr Leu Thr Cys Gly Leu Ser Ser Gly Ser Val Ser
145                 150                 155                 160
Thr Ser Tyr Tyr Pro Ser Trp Tyr Gln Gln Thr Pro Gly Gln Ala Pro
                165                 170                 175
Arg Thr Leu Ile Tyr Ser Thr Asn Thr Arg Ser Ser Gly Val Pro Asp
            180                 185                 190
Arg Phe Ser Gly Ser Ile Leu Gly Asn Lys Ala Ala Leu Thr Ile Thr
        195                 200                 205
Gly Ala Gln Ala Asp Asp Glu Ser Asp Tyr Tyr Cys Val Leu Tyr Met
    210                 215                 220
Gly Ser Gly Gln Tyr Val Phe Gly Gly Gly Thr Lys Leu Thr Val Leu
225                 230                 235                 240
Gly
```

<210> SEQ ID NO 21
<211> LENGTH: 6
<212> TYPE: PRT
<213> ORGANISM: Homo sapiens

<400> SEQUENCE: 21

```
His His His His His His
1               5
```

<210> SEQ ID NO 22
<211> LENGTH: 21
<212> TYPE: DNA
<213> ORGANISM: Homo sapiens

<400> SEQUENCE: 22
cagtctatgc ggccccattc a                                         21

<210> SEQ ID NO 23
<211> LENGTH: 21
<212> TYPE: DNA
<213> ORGANISM: Homo sapiens

<400> SEQUENCE: 23
atgaaatacc tattgcctac g                                         21

-continued

```
<210> SEQ ID NO 24
<211> LENGTH: 11
<212> TYPE: PRT
<213> ORGANISM: Homo sapiens

<400> SEQUENCE: 24

Ala Ala Ala Ser Gly Gly Pro Glu Gly Gly Ser
1               5                   10
```

HUMAN MINI-ANTIBODY CYTOTOXIC FOR TUMOR CELLS WHICH EXPRESS THE ERBB2 RECEPTOR

CROSS REFERENCE TO RELATED APPLICATIONS

This application is filed under 35 U.S.C. §371 and claims priority to International Application No. PCT/EP02/07671, filed Jul. 10, 2002, which application claims priority to Italian Application No. RM2001A000408, filed Jul. 10, 2001.

FIELD OF THE INVENTION

The present invention refers to a human mini-antibody cytotoxic for tumor cells that express the ErbB2 receptor, its corresponding sequence, the procedure for isolating it, and its use in therapy.

STATE OF THE ART

The ErbB2 transmembrane tyrosine kinase receptor (RTK), homologous to the epidermal growth factor receptor (EGFR) (1, 2), is highly expressed in breast, ovary and lung carcinomas (3, 4), as well as in salivary gland and gastric tumor-derived cell lines (5, 6). Its overexpression, which occurs most commonly via gene amplification, can reach as many as $2 \times 10^6$ molecules per cell. In normal tissues it is expressed at low levels only in certain epithelial cell types (7). ErbB2 plays a central role in tumor progression, since it potentiates and prolongs the signal transduction cascades elicited by ligand activation of other ErbB RTK receptors (8). Overexpression of ErbB2 may also increase resistance of tumor cells to host defenses by allowing them to evade the immune surveillance against neoplastic growth exerted by activated macrophages (9). The accessibility of ErbB2 on the cell surface, and its implication in the development of malignancy of these tumors make it an attractive target for immunotherapy.

Several research groups have isolated mouse and rat monoclonal antibodies (mAbs) directed against ErbB2 extracellular domain (10-12). Some of these mAbs from rodents have been shown to be endowed with antiproliferative effects on tumor cells (10-14). However, as a consequence of their non-human origin, the use of these mAbs as immunotherapeutic drugs is limited.

A clear progress in this area of research consisted in the development of the antibody humanization technology with the production of humanized versions of antibodies from rodents (15). These mAbs retain their specificity and binding affinity, but show reduced immunogenicity. In particular, a humanized version of an anti-ErbB2 receptor murine antibody (Herceptin) is in use as a drug for treatment of breast cancer (16, 17).

Antibody fragments (scFv—single chain variable Fragment) have been isolated from combinatorial libraries expressed on phages, using for selection purified antigens or peptides immobilized on artificial surfaces. The disadvantages of this type of approach is that it may lead to the selection of antibodies that do not recognize the antigen in its native state, i.e. in its physiological context (37). For example, an anti-ErbB2 scFv isolated by using the extracellular domain of purified ErbB2 was not capable of binding ErbB2 on the surface of SKBR3 cells (21).

On the contrary, direct panning (affinity selection on antigen) of an scFv repertoire on live cells has been shown to be essential for the isolation of antibodies that recognize cell surface antigens in their native configuration (38). Furthermore, this strategy allows for the identification of new cell surface antigens, which can be of use in diagnostics or therapy (22, 38-40).

Recently, it has been possible to isolate fully human scFv with the phage display technology. This is bsed on the expression of large repertoires of antibody domains on the capsids of filamentous phages, following their fusion to the phage coat protein pIII (18, 19). This methodology provides several advantages with respect to the hybridoma technology, which can be summarized as follows: (i) entirely human nature of the antibodies; (ii) possibility to bypass animal immunization; (iii) rapid isolation of scFv by affinity techniques from very large libraries of up to $10^{13}$ different clones; (iv) availability of stable scFv after phage selection, with high yields by expression in bacteria of the selected cDNAs; (v) possibility of obtaining antibodies when classical methodologies may not succeed, as with toxic antigens or highly conserved in various species.

The phage display technique has already been applied to the production of human scFv specific for ErbB2, using for their selection its isolated recombinant extracellular domain (20, 21), or more recently breast tumor cells (22). Given their high affinity for the receptor, these immunoreagents may be considered precious tools as delivery vehicles for specifically directing cytotoxic agents to antigen-bearing tumor cells. However, none of them has antitumor activity.

SUMMARY OF THE INVENTION

The object of the present invention is a fully human scFv, named Erbicin, specific for the ErbB2 receptor, with pharmacological, particularly antitumour, activity. Erbicin has been isolated from a very large phagemid library (Griffin.1 library) (19) of human synthetic scFv by panning (affinity selection on antigen) carried out on live cells that express different levels of ErbB2. It has been found that the single chain fragment of a human anti-ErbB2 antibody, called Erbicin, shows biological properties not described for other anti-ErbB2 scFv isolated so far. In fact Erbicin binds specifically to the ErbB2 receptor, it is internalized by target cells, it severely inhibits receptor phosphorylation, and displays a powerful growth inhibition of all ErbB2 positive cell lines tested. In addition, a clear cytotoxic effect was evidenced towards ErbB2 hyperexpressing SKBR3 cells, in which apoptotic death is induced. These features are present both in soluble Erbicin, and in its phage format (Ph-Erbicin).

Another object of the invention are the isolated sequences listed in the description, relative to the corresponding variants, mutants and portions. Particularly relevant are the portions present in bold type within the sequences.

Another object of the invention are the pharmaceutical compositions comprising as active principle Erbicin itself in its phage format (Ph-Erbicin), or Erbicin fused to constant regions from human antibodies, or to toxins, or to molecules with cytotoxic potential, such as enzymes with ribonuclease or protease activity (clearly known to the expert in the field).

Another object of the invention is the use of the scFv according to the invention in therapy, particularly as an antitumour agent, more particularly for the treatment of tumors in which cells express the ErbB2 receptor, such as cells from mammary, ovary or lung carcinomas.

Additional objects of the invention will be evident from the following detailed description of the invention.

BRIEF DESCRIPTION OF THE FIGURES

In FIG. 2B, FIG. 2D and FIG. 2F (corresponding to panels B, D and F respectively) cells were probed with anti-ErbB2 MgR6 mAb (shaded peaks), or with OKT3, a control, unrelated anti-CD3 mAb (unshaded peaks).

In FIG. 6B and FIG. 6D (corresponding to panels B and D respectively), the anti-proliferative effects of Ph-Erbicin ($2 \times 10^{10}$ cfu/ml, FIG. 6B corresponding to panel B) and Erbicin (20 µg/ml, FIG. 6D corresponding to panel D) on SKBR3 cells are expressed as the percentage of DNA synthesis in treated versus control cells. In control cells about $1.2 \times 10^3$ cpm of [$^3$H]thymidine were incorporated. Unrelated scFv (anti-NIP, anti-gp200-MR6), in their phage (Ph-) or soluble format, and phage lacking the scFv moiety (wt-phage) were tested as controls.

FIG. 7A (corresponding to Panel A), control cells; FIG. 7B (corresponding to panel B), cells treated for 72 h with Ph-Erbicin ($6 \times 10^{10}$ cfu/ml).

FIG. 8A, Elisa assays of hERB-RNase on SKBR3 cells (closed symbols), expressing high levels of the receptor, and on A431 cells (empty symbols), expressing very low levels; FIG. 8B, effects of ERB-RNase on the proliferation of SKBR3 (closed symbols) and A431 (empty symbols) cells. The dose-response curves refer to the percentage of alive cells treated for 72 h with the immunoagent versus non treated cells (about $3 \times 10^4$).

DETAILED DESCRIPTION OF THE INVENTION

Figure 1:
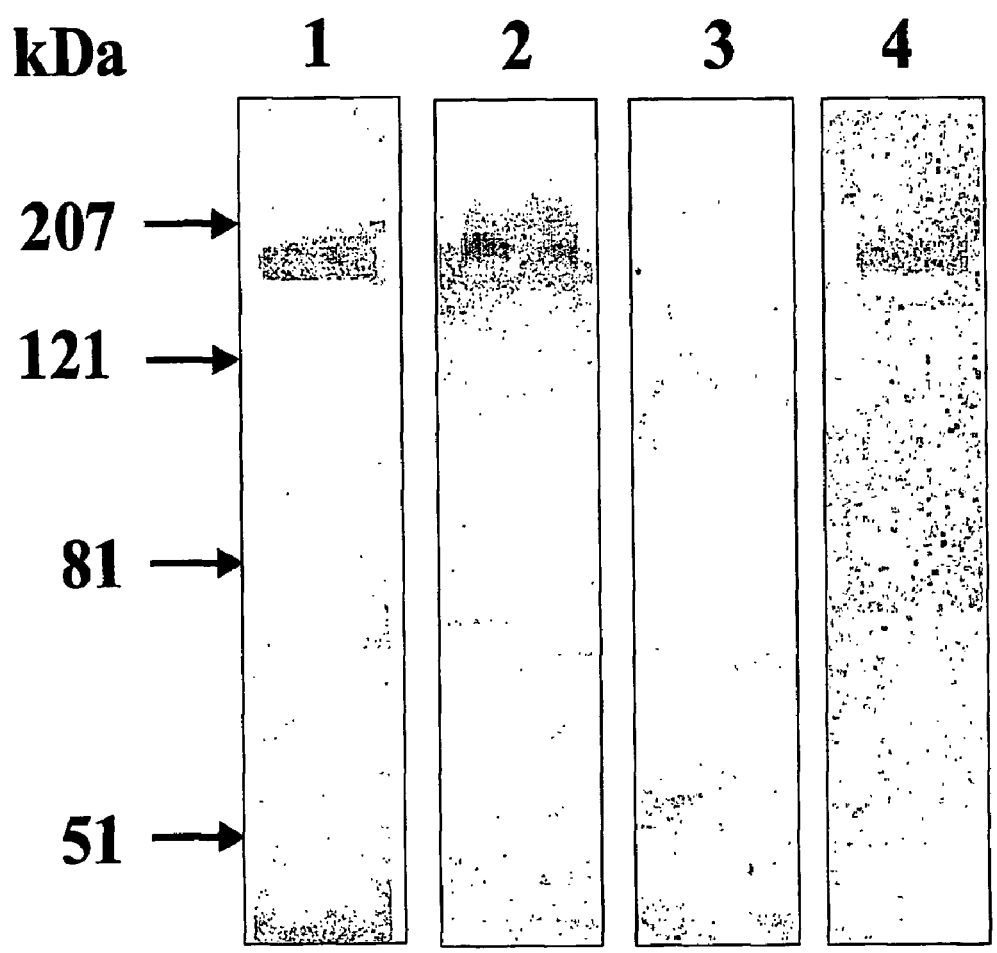
FIG. 1. Western blot analysis of cell extracts prepared from SKBR3 cells. Extracts were probed with: scFv displayed on phages (Ph-Erbicin) (lane 1); anti-ErbB2 MgR6 mAb (lane 2); anti-thyroglobulin scFv displayed on phages (lane 3). In lane 4, a cell extract from SKBR3 cells, previously immunoprecipitated with anti-ErbB2 MgR6 mAb, was probed with Ph-Erbicin.

The present invention refers to a fuilly human single chain miniantibody (scFv), which specifically binds to ErbB2, hence called anti-ErbB2 scFv, according to the nomenclature used for antibodies, well known to the expert in the field. This miniantibody has the property to bind to the ErbB2 receptor and engender the inhibition of its phosphorylation. This inhibition is of the order of 65% at least, when measured in SKBR3 cells by assays with anti-phosphotyrosine antibodies carried out on cell extracts pretreated at increasing time intervals (from 1 to 7 hours) with Erbicin, to detect the decrease of the phosphorylation level of the receptor. This is described in detail in the Examples in the present description. Said miniantibody has both cytostatic and cytotoxic effects on cells that express the ErbB2 receptor.

It is to be noted that in the herein below listed sequences, bold underlined sequences are relevant for the present invention. They correspond to CDRs, Complementary Determining Regions.

The miniantibody scFv described in the present invention has the following amino acid sequence, defined as SEQ ID. N. 20—Amino acid sequence of the miniantibody (ScFv):

QVQLLQSAAEVKKPGESLKISCKGSGYSFTSYWIGWVRQMPGKGLEWMGI

IYPGDSDTRYSPSFQGQVTISADKSISTAYLQWSSLKASDTAVYYCARWR

DSPLWGQGTLVTV-SSGGGGSGGGGSGGSAL-

QAVVTQEPSFSVSPGGTVTLTCGLSSGSVSTSYYPSWYQQTPGQAPRTLI

YSTNTRSSGVPDRFSGSILGNKAALTITGAQADDESDYYCVLYMGSGQYV

FGGGTKLTVLG encoded by the DNA SEQ ID. N. 19—DNA sequence of the miniantibody (ScFv):

5'-CAGGTGCAGCTGTTGCAGTCTGCAGCAGAGGTGAAAAAGCCCGGGGA

GTCTCTGAAGATCTCCTGTAAGGGTTCTGGATACAGCTTTACCAGCTACT

GGATCGGCTGGGTGCGCCAGATGCCCGGGAAAGGCCTGGAGTGGATGGGG

ATCATCTATCCTGGTGACTCTGATACCAGATACAGCCCGTCCTTCCAAGG

CCAGGTCACCATCTCAGCCGACAAGTCCATCAGCACCGCCTACCTGCAGT

GGAGCAGCCTGAAGGCCTCGGACACGGCCGTGTATTACTGTGCAAGATGG

```
CGTGATTCGCCTTTGTGGGGCCAAGGTACCCTGGTCACCGTC-TCGAGTG

GTGGAGGCGGTTCAGGCGGAGGTGGCTCTGGCGGTAGTGCACTT-CAGGC

TGTGGTGACTCAGGAGCCATCGTTCTCAGTGTCCCCTGGAGGGACAGTCA

CACTCACTTGTGGCTTGAGCTCTGGCTCAGTCTCTACTAGTTACTACCCC

AGCTGGTACCAGCAGACCCCAGGCCAGGCTCCACGCACGCTCATCTACAG

CACAAACACTCGCTCTTCTGGGGTCCCTGATCGCTTCTCTGGCTGCATCC

TTGGGAACAAAGCTGCCCTCACCATCACGGGGCCCAGGCAGATGATGAA

TCTGATTATTACTGTGTGCTGTATATGGGTAGTGGCCAGTATGTATTCGG

CGGAGGGACCAAGCTGACCGTCCTAGGT-3'
```

The present invention comprises all the nucleotide sequences that, for the degeneracy of the genetic code, can encode the present amino acid sequence, or the amino acid sequences containing conservative substitutions, i.e. determining amino acid substitutions with the same characteristics of polarity or steric hindrance of the corresponding in sequence ID N. 20, and the nucleotide sequences encoding said amino acid sequences containing conservative substitutions.

The following additional sequences are within the invention:

SEQ ID. N. 1—DNA sequence of VH region (variable region of the heavy chain):

```
5'-CAGGTGCAGCTGTTGCAGTCTGCAGCAGAGGTGAAAAAGCCCGGGGA

GTCTCTGAAGATCTCCTGTAAGGGTTCTGGATACAGCTTTACCAGCTACT

GGATCGGCTGGGTGCGCCAGATGCCCGGGAAAGGCCTGGAGTGGATGGGG

ATCATCTATCCTGGTGACTCTGATACCAGATACAGCCCGTCCTTCCAAGG

CCAGGTCACCATCTCAGCCGACAAGTCCATCAGCACCGCCTACCTGCAGT

GGAGCAGCCTGAAGGCCTCGGACACGGCCGTGTATTACTGTGCAAGATGG

CGTGATTCGCCTTTGTGGGGCCAAGGTACCCTGGTCACCGTC-3'
```

SEQ ID. N. 11 DNA sequence of region VL (variable region of the light chain):

```
5'-CAGGCTGTGGTGACTCAGGAGCCATCGTTCTCAGTGTCCCCTGGAGG

GACAGTCACACTCACTTGTGGCTTGAGCTCTGGCTCAGTCTCTACTAGTT

ACTACCCCAGCTGGTACCAGCAGACCCCAGGCCAGGCTCCACGCACGCT

CATCTACAGCACAAACACTCGCTCTTCTGGGGTCCCTGATCGCTTCTCTG

GCTCCATCCTTGGGAACAAAGCTGCCCTCACCATCACGGGGCCCAGGCA

GATGATGAATCTGATTATTACTGTGTGCTGTATATGGGTAGTGGCCAGTA

TGTATTCGGCGGAGGGACCAAGCTGACCGTCCTAGGT-3'
```

SEQ ID. N. 9 DNA sequence of the "LINKER" (region connecting VH and VL):

```
5'-TCGAGTGGTGGAGGCGGTTCAGGCGGAGGTGGCTCTGGCGGTAGTGC

ACTT-3'
``` and the corresponding amino acid sequences are respectively the following:

SEQ ID. N. 2: Amino acid sequence of VH region (variable region of the heavy chain):

```
QVQLLQSAAEVKKPGESLKISCKGSGYSFTSYWIGWVRQMPGKGLEWMGI

IYPGDSDTRYSPSFQGQVTISADKSISTAYLQWSSLKASDTAVYYCARWR

DSPLWGQGTLVTV
```

SEQ ID. N. 12—Amino acid sequence of region VL (variable region of the light chain):

```
QAVVTQEPSFSVSPGGTVTLTCGLSSGSVSTSYYPSWYQQTPGQAPRTLI

YSTNTRSSGVPDRFSGSILGNKAALTITGAQADDESDYYCVLMGSGQYVF

GGGTKLTVLG
``` and SEQ ID. N. 10—Amino acid sequence of the "LINKER" (peptide connecting VH and VL):

```
SSGGGGSGGGGSGGSAL
```

The regions in bold type within sequences SEQ ID N. 1 and SEQ ID N. 11 correspond to sequences coding for CDR-1, CDR-2 and CDR-3 of VH and VL chains, and are indicated respectively, as:

SEQ ID. N. 3—DNA sequence of CDR-1 region of VH chain:

```
5'-AGCTACTGGATCGGC-3'
```

SEQ ID. N. 5—DNA sequence of CDR-2 region of the VH chain:

```
5'-ATCATCTATCCTGGTGACTCTGATACCAGATACAGCCCGTCCTTCCA

AGGC-3'
```

SEQ ID. N. 7—DNA sequence of CDR-3 region of VH chain:

```
5'-TGGCGTGATTCGCCTTTG-3'
```

SEQ ID. N. 13—DNA sequence of CDR-1 region of VL chain:

```
5'-GGCTTGAGCTCTGGCTCAGTCTCTACTAGTTACTACCCCAG-3'
```

SEQ ID. N. 15—DNA sequence of CDR-2 region of VL chain:

```
5'-AGCACAAACACTCGCTCTTCT-3'
``` and SEQ ID. N. 17—DNA sequence of CDR-3 region of VL chain:

```
5'-GTGCTGTATATGGGTAGTGGCCAGTATGTA-3'
```

As previously published (49), CDR regions (Complementarity Determining Regions) correspond to the regions that concur to define the contact site between antigen and antibody. Thus, they are specifically involved in binding speci ficity. The corresponding amino acid sequences are indicated as:

SEQ ID. N. 4—Amino acid sequence of CDR-1 region of VH chain:

SYWIG

SEQ ID. N. 6—Amino acid sequence of CDR-2 region of VH chain:

IIYPGDSDTRYSPSFQG

SEQ ID. N. 8—Amino acid sequence of CDR-3 region of VH chain:

WRDSPL

SEQ ID. N. 14—Amino acid sequence of CDR-1 region of VL chain:

GLSSGSVSTSYYPS

SEQ ID. N. 16—Amino acid sequence of CDR-2 region of VL chain:

STNTRSS

SEQ ID. N. 18—Amino acid sequence of CDR-3 region of VL chain:

VLYMGSGQYV

In particular, the linker is a peptide fragment or peptide, for example long about 15 amino acid residues, in preference comprising glycine residues.

Homologous DNA sequences with at least 60% identity, preferably 80%, even more preferably 90% with each of the following sequences: (SEQ ID. N. 1, 3, 5, 7, 9, 11, 13, 15, 17, 19) or the homologous amino acid sequences identical by at least 40%, preferably 60%, or even more preferably 80-90% with respect to the amino acid sequences (SEQ ID. N. 2, 4, 6, 8, 10, 12, 14, 16, 18, 20) indicated for the present invention.

In particular, there are to be considered within the scope of the present invention all the mutations in the DNA sequences (SEQ ID. N. 1, 3, 5, 7, 9, 11, 13, 15, 17, 19) capable of determining conservative substitutions in the proteins with sequences (SEQ ID. N. 2, 4, 6, 8, 10, 12, 14, 16, 18, 20).

An additional aspect of the invention is the use of such DNA sequences, in particular of those encoding VH; VL and CDR-1-2 and -3 VH and CDR-1, -2 and -3 VL for the construction of chimeric proteins and fusion proteins, of which the above amino acid sequences represent the portion endowed with binding specificity, or capable of confer such specificity.

Within the scope of the present invention there are the fusion proteins comprising at least two distinct functional regions, one of which made up of the VH, or the VL region, or of both VH and VL, or SEQ ID N. 20.

It is part of the invention the procedure for the isolation of the human anti-ErbB2 scFv from a phage, library of antibody fragments of human origin (Griffin 1.). The identified miniantibody shows an intrinsic, strong and selective anti-proliferative activity on cells that overexpress ErbB2. It has been isolated through a selection performed on a phage library panning with the antigen expressed in vivo live cells overexpressing the ErbB2 antigen. The selection strategy was based on the use of two combinations of cell lines, each comprising an ErbB2-positive and an ErbB2-negative cell line. By this approach, it has been found that the scFv expressed on phage (called Ph-Erbicin) recognized specifically the ErbB2 receptor with no crossed reactivity with the structurally related EGFR (ErbB1), expressed at high levels on A431 cells (Table I). It is to be underlined that the isolated scFv could discriminate ErbB2 from all other members of the ErbB family, such as ErbB3 and ErbB4, expressed at very low levels on cell lines SK-OV-3 and SKBR3, respectively.

The anti-ErbB2 scFv (miniantibody) has been obtained also in soluble form as a pure protein from the periplasmic extract of bacterial cells infected with the positive phage clone. It has been found that the anti-ErbB2 scFv in its soluble form, called Erbicin, maintains its binding specificity to the receptor.

It has been found that Ph-Erbicin and Erbicin are rapidly internalized by endocytosis in cells that overexpress ErbB2. Furthermore, both the immufioreagents show a strong anti-proliferative effect on ErbB2-positive cell lines, and the corresponding degree of their antitumor activity is correlated to ErbB2 expression level on cell surfaces (Table I). No effects have been detected on ErbB2-negative cell lines.

It has been found that Ph-Erbicin has an anti-proliferative effect (cytostatic) on all ErbB2-positive tumor cells, whereas its effect on SKBR3 is cytotoxic, with the induction of apoptosis. The mechanism which is the basis of this high sensitivity of SKBR3 cells to anti-ErbB2 immunoreagents appears to depend on an autocrine activation loop, in turn dependent on the overexpression not only of the ErbB2 receptor, but also of its ligand. This loop would be interrupted by the anti-ErbB2 scFv.

Ph-Erbicin is the first example of human scFv expressed on phage, with a dose-dependent cytostatic/cytotoxic action. In fact, the anti-ErbB2 scFv here reported has been found to be more active as an antitumor agent when it is expressed on phage, than in its soluble format. Likely, the scFv expressed on phage is more stable, and/or it acquires a different conformation that increases its biological effects. Alternatively, although most phage express a single scFv, we cannot exclude the possibility that some phage express more copies of the scFv fragments. This increase in antibody valence may explain the higher efficacy of the scFv in phage format.

In any case the human anti-ErbB2 scFv, according to the invention, is capable, both in its soluble and phage formats, to be effectively internalized by target cells overexpressing ErbB2, and to specifically inhibit their growth, or to generate a cytotoxic effect. Given its fillly human origin, soluble Erbicin would not be immunogenic in human patients; hence it represents an ideal active principle for anti-neoplastic therapy in which tumor cells express the ErbB2 receptor, such as cells from mammary, ovary, and lung carcinomas.

Furthermore, both Ph-Erbicin and Erbicin, for their effective internalization by target cells, can be used as vehicles to direct drugs or toxins (known to the expert) to the cytosol of tumor target cells. This should increase the antitumor potential of the transported molecules, fused in chimeras with the scFv, and should decrease their possible systemic toxicity.

The pharmaceutical compositions according to the invention comprise as active principle an effective amounts of Erbicin, soluble or in phage format; Erbicin as a protein fused to constant regions from human antibodies, or to toxins or molecules with cytotoxic potential, such as enzymes with ribonuclease or protease activity.

In this respect we have already prepared: 1. a fully human fusion protein, called ERB-Ab, made up of Erbicin fused to the constant regions from human immunoglobulins G1; 2. an ImmunoRNase, i.e. a fully human fusion protein, called hERB-RNase, made up of Erbicin fused to a human enzyme with ribonuclease activity (human pancreatic ribonuclease).

Erb-Ab is virtually a fully human antibody, capable to recognize specifically ErbB2-positive tumor cells and selectively kill them. It represents a potentially more effective anti-cancer drug than the corresponding single chain antibody fragment (Erbicin). Due to its larger size and the presence of an Fc portion, Erb-Ab is expected to have a longer half-life in human body fluids, and a stronger cytotoxic effect on target cells, attained by the activation of ADCC (antibody-dependent cellular cytotoxicity) and CDCC (complement-dependent cellular cytotoxicity) reactions. The ERB-Ab preparation was obtained through the following basic steps: (i) isolation of Erbicin encoding cDNA; (ii) fusion of said cDNA to a cDNA encoding the constant regions (CH2 and CH3) and the hinge peptide from human heavy chains of immunoglobulin G1, cloned in the expression vector plgplus (Novagen). The standard methodology (50) described for similar fusion reactions of scFv molecules to constant antibody regions was followed; (iii) expression of the resulting fusion cDNA in eucaryotic cells (P3X from a murine myeloma).

The ImmunoRNase hERB-RNase was obtained through the following basic steps: (i) fusion of the cDNA encoding Erbicin to the cDNA encoding human pancreas RNase. A DNA fragment encoding a spacer peptide of 11 amino acid residues (AAASGGPEGGS SEQ ID N. 24) was interposed between the two coding regions; (ii) expression of the resulting fusion cDNA in *Escherichia coli*; (iii) isolation and characterization of the recombinant protein. Its structural and functional characterization indicated that: (i) it specifically recognizes receptor-positive cells; (ii) it is endowed with enzymatic (ribonucleolytic) activity, (iii) tested on receptor-positive and -negative cell lines it specifically kills receptor-positive cells, hence it is capable of discriminating between target and non-target cells. hERB-RNase is the first fully human Immuno-RNase, i.e. a chimeric protein made up of a human antibody moiety fused to a human ribonucleolytic enzyme.

For its human nature, hERB-RNase is expected to be well tolerated in humans, because it is not immunogenic and not toxic, as the ribonuclease becomes toxic only when vehiculated into a target cell. Since it contains an antibody moiety highly specific for tumor cells that express the ErbB2 receptor, hERB-RNase represents a promising new anticancer drug for mammary, colon, ovarian and other carcinomas. To date, a single antibody-based anti-cancer drug is used in therapy, by the commercial name of Herceptin. This however, is a "humanized" murine molecule. The Erbicin-based immunoRNase is instead fullly human, and in fact the first fully human antibody-based anticancer agent.

The pharmaceutical compositions according to the invention fiurer comprise additives, diluents, adjuvants and eccipients known to the expert in the field. Also dosages and the administration protocols are fimctional to the subject and type of disease to be treated.

There are to be considered within the scope of the present inventions the expression and cloning vectors comprising the DNA sequences corresponding to SEQ ID. N. 1, 3, 5, 7, 9, 11, 13, 15, 17, 19, and their equivalent or homologous sequences useful for transfecting procaryotic or eucaryotic cells with the purpose of obtaining the expression of DNA or amino acid sequences indicated as SEQ ID. N. 2, 4, 6, 8, 10, 12, 14, 16, 18, 20, or their equivalent or homologous sequences, and those comprising conservative substitutions. To optimize or facilitate the purification of the recombinant miniantibodies or of the protein sequences described in the present invention, these may contain "tag," regions, e.g. obtained by expression of the corresponding DNA sequences fused in frame with the described proteins. An example of "tag" sequence is the polyhistidine sequence (HHHHHH SEQ ID N. 21), which allows for the purification of recombinant translates on affinity columns for heavy metals.

There are is also to be considered within the scope of the invention kits containing means for the preparation of Erbicin, soluble or in phage format or fused as mentioned in the above. This kits comprise means for preparing Erbicin and its derivatives or fusion forms according to the present application. Those means may include: possible means for the recovery of Erbicin and/or corresponding derivatives from periplasmic extracts; appropriate buffer, wash and conservation solutions; means for preparing a culture medium for the Erbicin, and complements for the culture medium such as glucose and IPTG as inducer.

A skilled person can easily identify the additives suitable in the kits reported above, among those chemically compatible additives known in the art.

Within the invention are also trausgenic animals containing genetically modified sequences with least one of the DNA sequences identified with SEQ ID. N. 1, 3, 5, 7, 9, 11, 13, 15, 17, 19, or equivalent or homologous sequences.

The antibodies and the proteins, as well as the vectors according the present invention, may be prepared conveniently as kits and used for diagnosis or therapy.

The present invention will be herein illustrated by descriptive, not limiting, examples with reference to the attached Figures.

EXAMPLE 1

Parallel Selection on Different Cell Lines to Isolate a Human, ErbB2 Specific scFv.

The strategy devised for the isolation of an anti-ErbB2 scFv from the Griffin.1 library (19) consisted in a double selection, with the use of two different combinations of "positive", i.e. antigen-bearing, and "negative" cell lines. In the first combination, NIH 3T3 cells transfected with DNA encoding human ErbB2 (23) were used as antigen-positive cells, and untransfected NIH 3T3 as antigen-negative cells. In the second combination, a human breast cancer cell line, naturally expressing high levels of ErbB2 receptor (SKBR3 cells), and a human epidermoid carcinoma cell line (A431 cells), expressing the receptor at very low levels, were used as antigen-positive and antigen-negative cells, respectively. The strategy of using two combinations of positive and negative cell lines was devised to guarantee an effective selection of the anti-ErbB2 clones.

In each selection round, a mixture of "positive" cells (about 10%), previously labeled with a fluorochrome, and unlabeled "negative" cells (90%) were incubated with the antibody phage display library ($10^{13}$ cfu per selection). The negative cells were used to deplete the library of phage antibodies that bound to common antigens. After 16 h of incubation at 4° C., cells were washed, and the labeled ones (about $1\times10^6$ cells) were isolated by fluorescence activated cell sorting (FACS). Phages bound to the cell surface were displaced ($1\times10^7$ cfu) and used to infect the *E. coli* TG1 bacterial strain. Initially, two rounds of selection were performed with SKBR3 and A431 cell lines. Positive phages, which selectively bound to the ErbB2 positive cell line, were submitted to two further rounds of selection, using either the same cell combination (strategy 1), or the NIH 3T3 transfected and untransfected cell lines (strategy 2). Strategy 2 was implemented to verify the possibility of recruiting phages with higher binding affinity by using cells that express lower levels of ErbB2.

From the last selection round of strategies 1 and 2, a total of forty clones were isolated, and identified as ErbB2-positive clones by ELISA screening, performed on both cell combinations.

The DNA encoding the variable regions of these positive clones was amplified by PCR, and then analyzed by digestion with BstNI and BsaJI restriction enzymes. Two different digestion patterns were obtained (named type A and B); these were seen in clones isolated by either strategy 1 or strategy 2. The sequence analysis of DNA encoding the variable regions of multiple selected clones, representative of each restriction pattern, identified two different cDNA sequences, coding for two novel human scFv. The finding that these scFv were selected independently by the use of two different combinations of antigen-positive and -negative cell lines led us to consider them as possible candidates of scFv specific for ErbB2.

Sequence analyses of multiple A- and B-type positive clones indicated that the heavy chain variable region (VH) of type A scFv belonged to the VH5 family (derived from the VH germline gene DP-73), whereas the VH region of type B scFv belonged to the VH3 family (derived from the DP-38 gene). The light chain variable region (VL) of type A and B scFv was found to belong to families VL8 (derived from the VL germline gene DPL-21) and VL1 (gene DPL-3), respectively.

Representative clones of type A and B were used for further analyses.

EXAMPLE 2

Characterization of Phage Antibodies Specificity.

To verify whether these clones were indeed specific for ErbB2, they were analyzed in their phage format by Western blotting performed on antigen-rich cell extracts prepared from the SKBR3 cell line. As shown in FIG. 1, positive scFv displaying phages (N.B. eliminare: from clone AD recognized a protein of approximately 185 kDa, the molecular weight expected for the ErbB2 antigen. In the same experiment, a protein corresponding to the same molecular size was recognized by the murine MgR6 mAb (24) known to be directed against ErbB2 (25, 26). No positive bands were detected when an anti-thyroglobulin scFv phage preparation was used as a negative control (see FIG. 1). Notably, a positive band of the expected molecular weight was also obtained (see FIG. 1) when the Western blotting was performed with the A type phage clone on ErbB2 previously isolated from SKBR3 cell extracts by immunoprecipitation with the anti-ErbB2 MgR6 mAb.

These results confirm unequivocally that the scFv from the type A clone bound specifically to ErbB2. As the type B clone recognized ErbB2 protein band, but also additional proteins in the cell lysate (data not shown), further analyses were performed on clone A, designated as Ph-Erbicin (scFv in its Phage format).

Ph-Erbicin was tested by flow cytometry for its ability to bind to a panel of human tumor cell lines expressing high levels of ErbB2. Cell lines that had not been previously used in the phage isolation procedure were chosen. Cells were incubated with Ph-Erbicin, washed twice with PBS, and treated with a murine mAb directed against the M13 phage. For detection, a rabbit anti-mouse fluoresceinated IgG was used.

Figure 2:
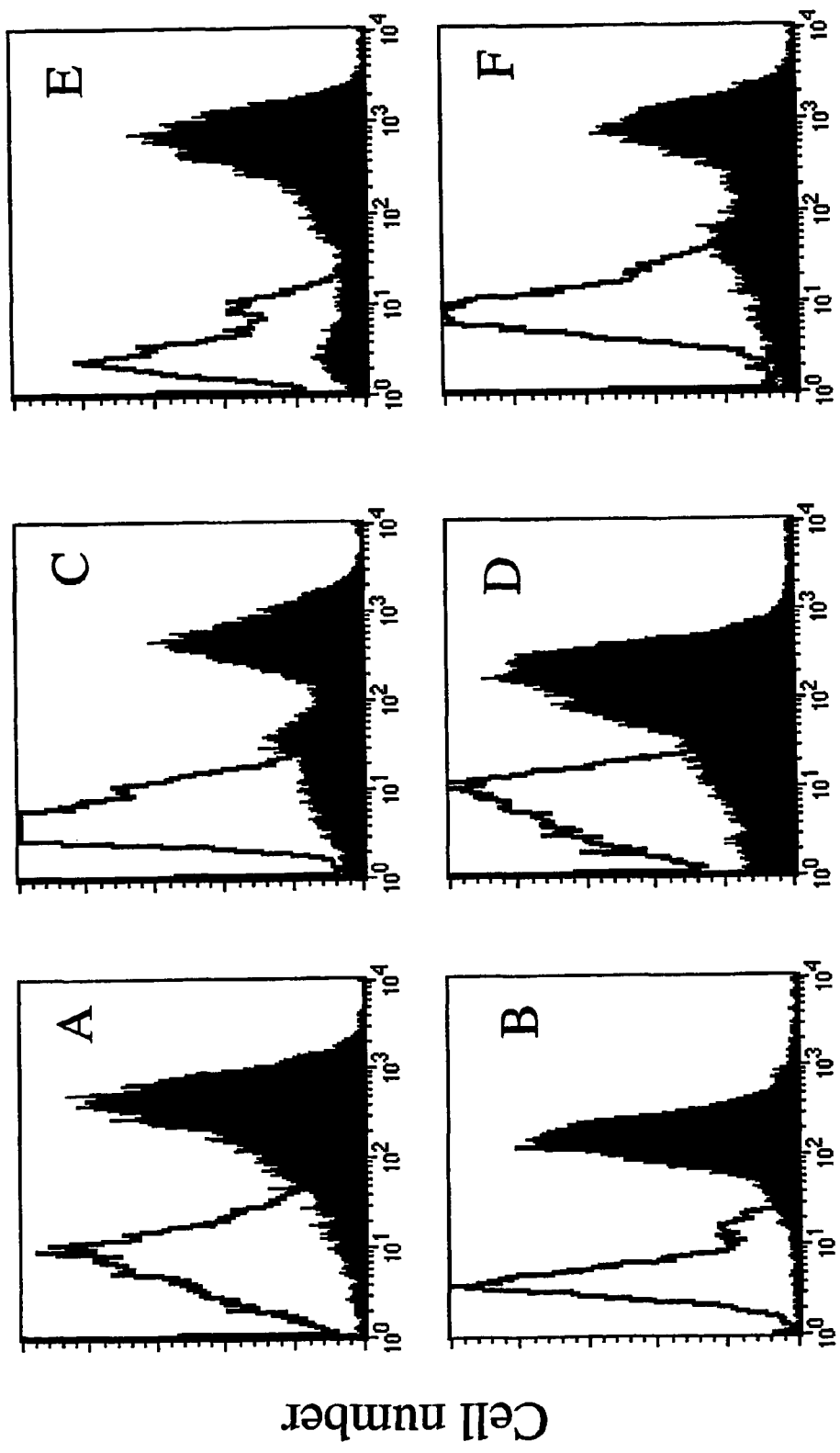
FIGS. 2A, 2B, 2C, 2D, 2E and 2F. Flow cytometric analysis of Ph-Erbicin binding to ErbB2 expressing cell lines: MDA-MB453 (FIG. 2A and FIG. 2B corresponding to panels A and B respectively); BT-474 (FIG. 2C and FIG. 2D corresponding to panels C and D respectively); SK-OV-3 (FIG. 2E and FIG. 2F corresponding to panels E and F respectively). Cells were probed with Ph-Erbicin (FIG. 2A, FIG. 2C and FIG. 2E corresponding to panels A, C and E respectively, shaded peaks) or with a control anti-NIP scFv displayed on phages (unshaded peaks).

As shown in FIG. 2 (panels A, C and E) and in Table I, Ph-Erbicin gave strong labeling of MDA-MB453 and BT-474 cells from breast carcinoma, and of SK-OV-3 cells from ovarian adenocarcinoma. On the contrary, no fluorescence was detected when the same cells were incubated with an irrelevant anti-NIP scFv-phage (27). The labeling intensity produced by Ph-Erbicin was comparable to that obtained with the anti-ErbB2 murine MgR6 mAb (FIG. 2, panels B, D and F).

Positive results were also obtained with SKBR3 and ErbB2-transfected NIH 3T3 cells probed with Ph-Erbicin, whereas no binding was detected either to ErbB2-untransfected NIH 3T3 cells, or to the A431 cell line (see Table I) that express ErbB2 at low levels (28, 29). It should be noted that the A431 cells express the homologous EGF receptor at high levels ($2\times10^6$ receptors per cell) (30, 31).

These results demonstrate that Ph-Erbicin: (i) can discriminate between ErbB2-expressing and non-expressing cell lines; (ii) specifically recognizes the ErbB2 extracellular domain; and (iii) discriminates between ErbB2 and EGFR receptors in spite of their extensive sequence identity.

Moreover, the data suggest a positive correlation between the extent of binding of Ph-Erbicin to ErbB2-positive cells and the levels of ErbB2 expression in these cell lines. This was determined by the results obtained with the anti-ErbB2 MgR6 mAb (see Table I). As MgR6 effectively titrates ErbB2 on the cell surface, the fluorescence data obtained with this mAb represent a measure of the expression levels of the receptor on the cell lines tested.

EXAMPLE 3

Expression and Characterization of Soluble Erbicin.

To prepare human anti-ErbB2 scFv from type A clone as a soluble molecule, the pHEN2 phagemid vector (a derivative of the pHEN1 vector (27)) containing the DNA encoding Erbicin, was used to transform the bacterial strain SF110 (32). After induction with IPTG, a periplasmic extract was prepared as previously described (33).

To verify whether the soluble anti-ErbB2 scFv retained the binding properties of the scFv displayed on phages, the periplasmic extract was analyzed by ELISA, as well as by flow cytometry using the cell lines tested with Ph-Erbicin. The results from both analyses showed that the anti-ErbB2 soluble scFv selectively binds to the antigen-bearing cells (data not shown). In its soluble format the scFv immunoreagent was named Erbicin.

Figure 3:
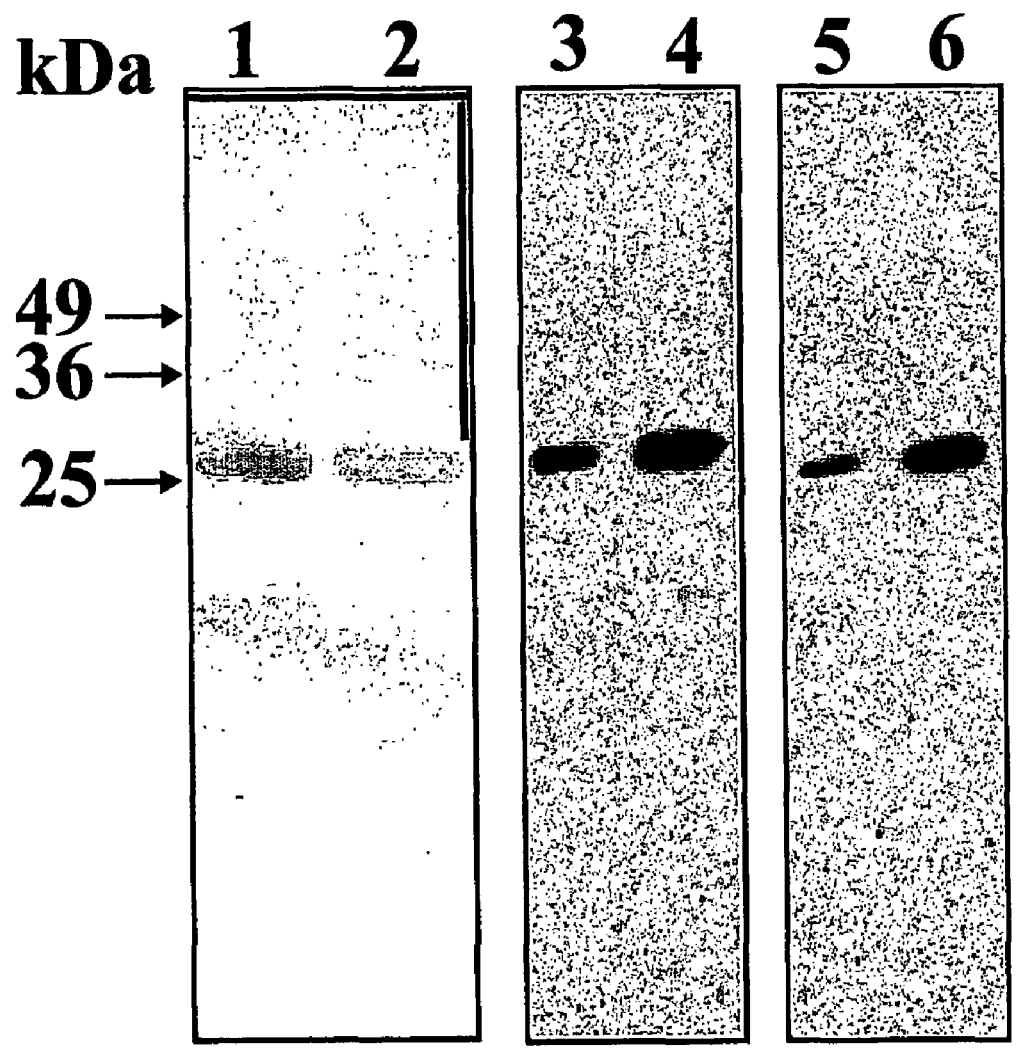
FIG. 3. SDS-gel electrophoresis and Western blot analyses of Erbicin. Lanes 1 and 2: Coomassie staining of Erbicin and control anti-NIP soluble scFv, respectively. In lanes 3 to 6 Western blot analyses are shown of Erbicin (Ganes 3 and 5) and anti-NIP scFv (lanes 4 and 6) probed with anti-myc 9E10 mAb (lanes 3 and 4) or with anti-His mAb (lanes 5 and 6).

Since the scFv encoding cDNA is cloned into the pHEN2 vector fused to a C-terminal hexahistidine sequence (SEQ ID N. 21), the recombinant Erbicin was purified by immobilized-metal affinity chromatography (IMAC) by using Ni-NTA agarose, and then analyzed by SDS-PAGE electrophoresis. A single band of the expected molecular size (about 27 kDa) was obtained by Blue Coomassie staining (FIG. 3). The purified Erbicin was also analyzed by Western blotting either with an anti-His tag mAb, or with the 9E10 anti-myc mAb (directed against a 11-residue peptide from the myc protein fused to the C-terminal end of the scFv). By both analyses a band of the expected size, approximately 27 kDa, was visualized (FIG. 3).

EXAMPLE 4

Internalization of Ph-Erbicin and Erbicin by SKBR3 Cells.

The new human anti-ErbB2 scFv was then tested, both in the phage and in the soluble format, for its ability to undergo receptor-mediated endocytosis in SKBR3 cells. To test the immunoreagent in the phage format, cells grown on coverslips were incubated with Ph-Erbicin ($10^{11}$ cfu/ml) for 16 hours at 37° C. Cells were then extensively washed with PBS to remove non-specific binding, followed by four washes with a high salt and low pH stripping glycine buffer to remove phages specifically bound to the cell surface (34). Cells were then fixed and permeabilized, and internalized phages were visualized with an anti-M13 mAb, followed by a rabbit anti-IgG from mouse FITC-conjugated. As a control, an anti-NIP scFv-phage preparation ($10^{12}$ cfu/ml) was used.

Figure 4:
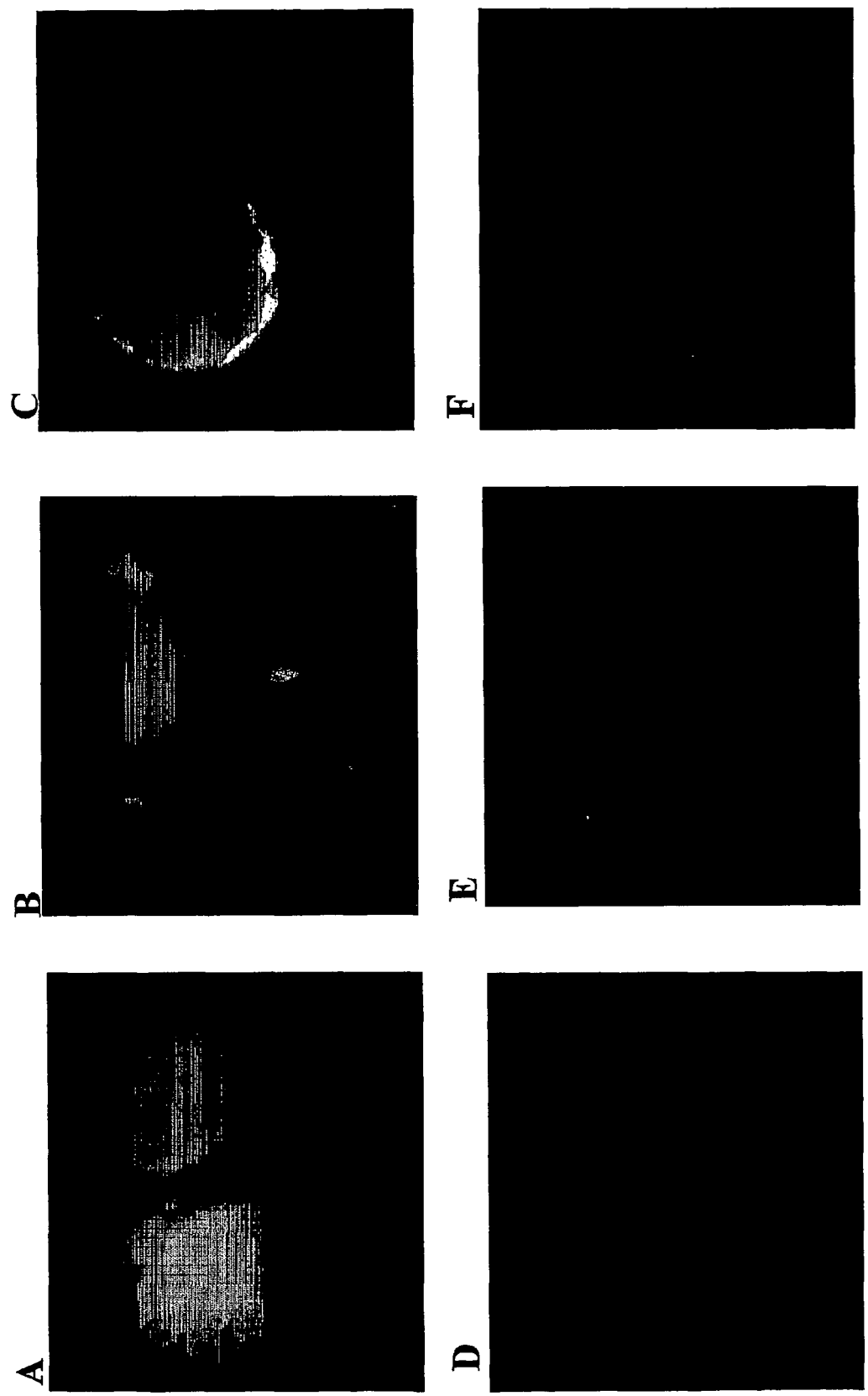
FIGS. 4A, 4B, 4C, 4D, 4E and 4F. Internalization of Ph-Erbicin and Erbicin in SKBR3 cells as visualized by confocal microscopy. Cells were incubated for 16 hours with Ph-Erbicin (FIG. 4A corresponding to panel A), or with Erbicin for 2 h (FIG. 4B corresponding to panel B) or 16 h (FIG. 4C corresponding to panel C). Anti-NIP scFv displayed on phages (FIG. 4D corresponding to panel D) or soluble anti-NIP scFv (FIG. 4E and FIG. 4F corresponding to panels E and F respectively) were used in parallel as controls. Magnification 1:1000.

By confocal microscopy a strong intracellular staining was observed for Ph-Erbicin, whereas no staining was detected with the anti-NIP scFv-phage (see FIG. 4, panels A and D). To determine whether infectious antibody-equipped phage particles could be recovered from within the cells, the experiment was repeated on cells grown in 6-well plates, then incubated with the antibody carrying phages for 2 hours at 37° C. After the last stripping wash, cells were dissociated from the culture plates by trypsinization, washed three times with PBS and then lysed with 100 mM triethylamine (TEA). Phage particles, recovered in the cell lysates, were titrated by infection of E. coli TG1 strain, as previously described (34). The titer of Ph-Erbicin in the TEA fraction was much higher (at least one order of magnitude) than that obtained using an anti-thyroglobulin scFv-phage as a control (data not shown).

These results indicate that there is a strict correlation between endocytosis of phage particles and high antigen specificity of the scFv displayed on phages.

To determine whether soluble Erbicin-A7 was also effectively internalized, the scFv was incubated with SKBR3 cells grown on coverslips for 2 or 16 hours at 37° C. The intracellular scFv was identified by confocal microscopy using anti-myc 9E10 mAb, followed by rabbit anti-mouse FITC-conjugated antibody. When incubated with Erbicin, a strong intracellular fluorescence was visualized (FIG. 4, panels B and C), whereas no staining was detected upon incubation for the same time periods with an irrelevant anti-NIP soluble scFv (FIG. 4, panels E and F), expressed and purified as described for Erbicin.

EXAMPLE 5

Effects on Tyrosine Phosphorylation of ErbB2.

Figure 5:
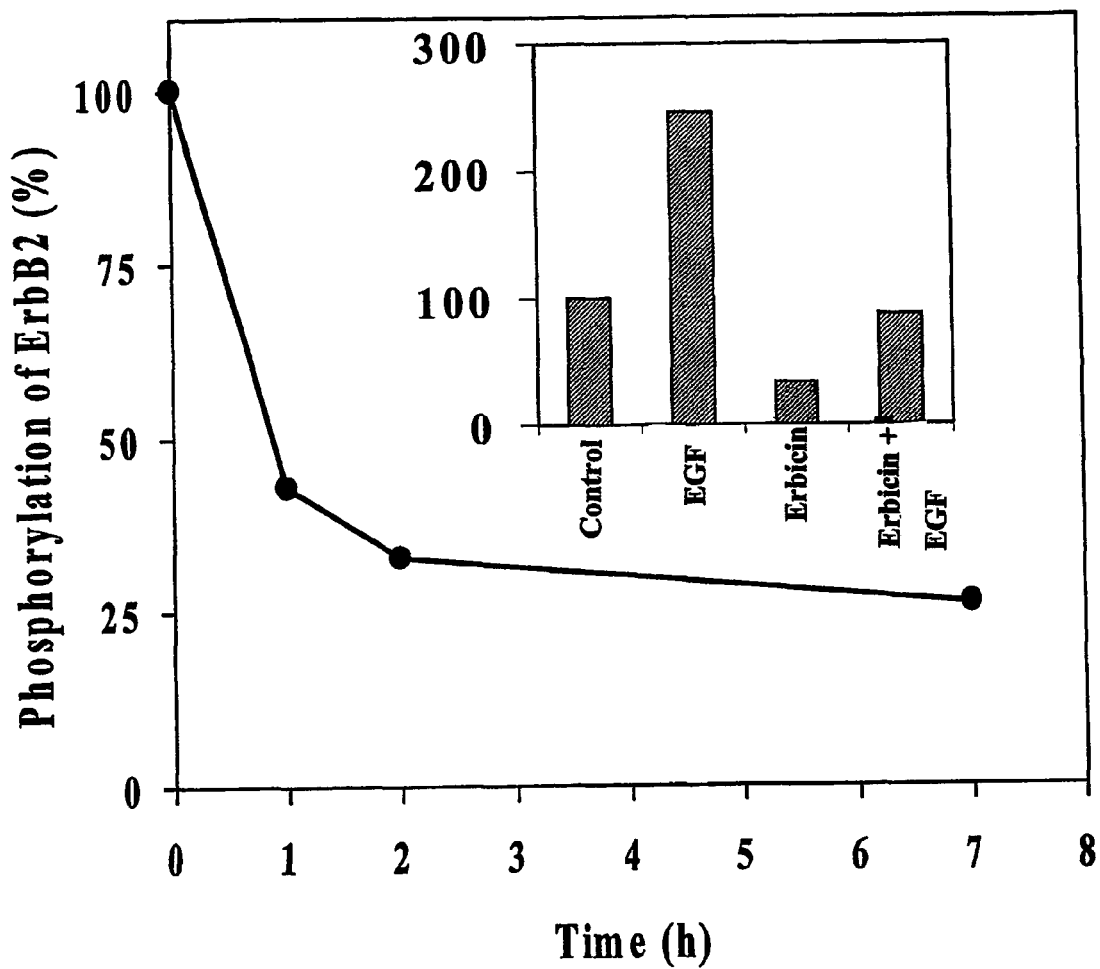
FIG. 5. The effects of Erbicin-A7 on ErbB2 phosphorylation. The levels of ErbB2 phosphorylation in extracts from SKBR3 cells, treated for the indicated times with Erbicin (12 µg/ml), are reported as percentages of the phosphorylation level detected in untreated cells. In the insert, the effects are shown of: a 2 h treatment with Erbicin (12 µg/ml); a 15 mnin treatment with EGF (100 ng/ml); the same treatment with EGF on cells previously treated for 2 h with Erbicin-A7. A control consisted of untreated cells.

Since tyrosine kinase receptors are activated by ligand binding with an increase in phosphorylation of tyrosine in the C-terminal domain, we tested the effects of Erbicin on ErbB2 phosphorylation. SKBR3 cells starved for 16 h were treated for increasing time periods at 37° C. with Erbicin (12 µg/ml). Cell were lysed and equivalent aliquots from the extracts were analyzed by parallel Western blottings, using either a mAb specific for phosphotyrosine (P-Tyr mAb), or anti-ErbB2 MgR6 mAb. Both analyses were performed in the presence of an anti-actin mAb to directly compare the levels of ErbB2 receptor with those of tyrosine phosphorylation. The signal intensity of positive bands was estimated by phosphorimaging. In FIG. 5, the effects of Erbicin on ErbB2 phosphorylation are shown. A strong inhibitory effect on phosphorylation was already detectable after a 1 h treatment, and after 7 h the inhibition reached 74% in comparison to the untreated cells. In the same experiment EGF, used as a positive control, effectively stimulated the phosphorylation of ErbB2, (see inset of FIG. 5). This stimulatory effect of EFG was significantly reduced when cells were previously incubated with Erbicin (see inset of FIG. 5).

EXAMPLE 6

Effects on Tumor Cell Proliferation.

It has been shown that some anti-ErbB2 mAbs are internalized and down-regulate ErbB2 expression, which could result in cell growth inhibition (4, 35). Since both Ph-Erbicin and Erbicin-A7 are internalized, their effects on target cell proliferation were tested.

Figure 6:
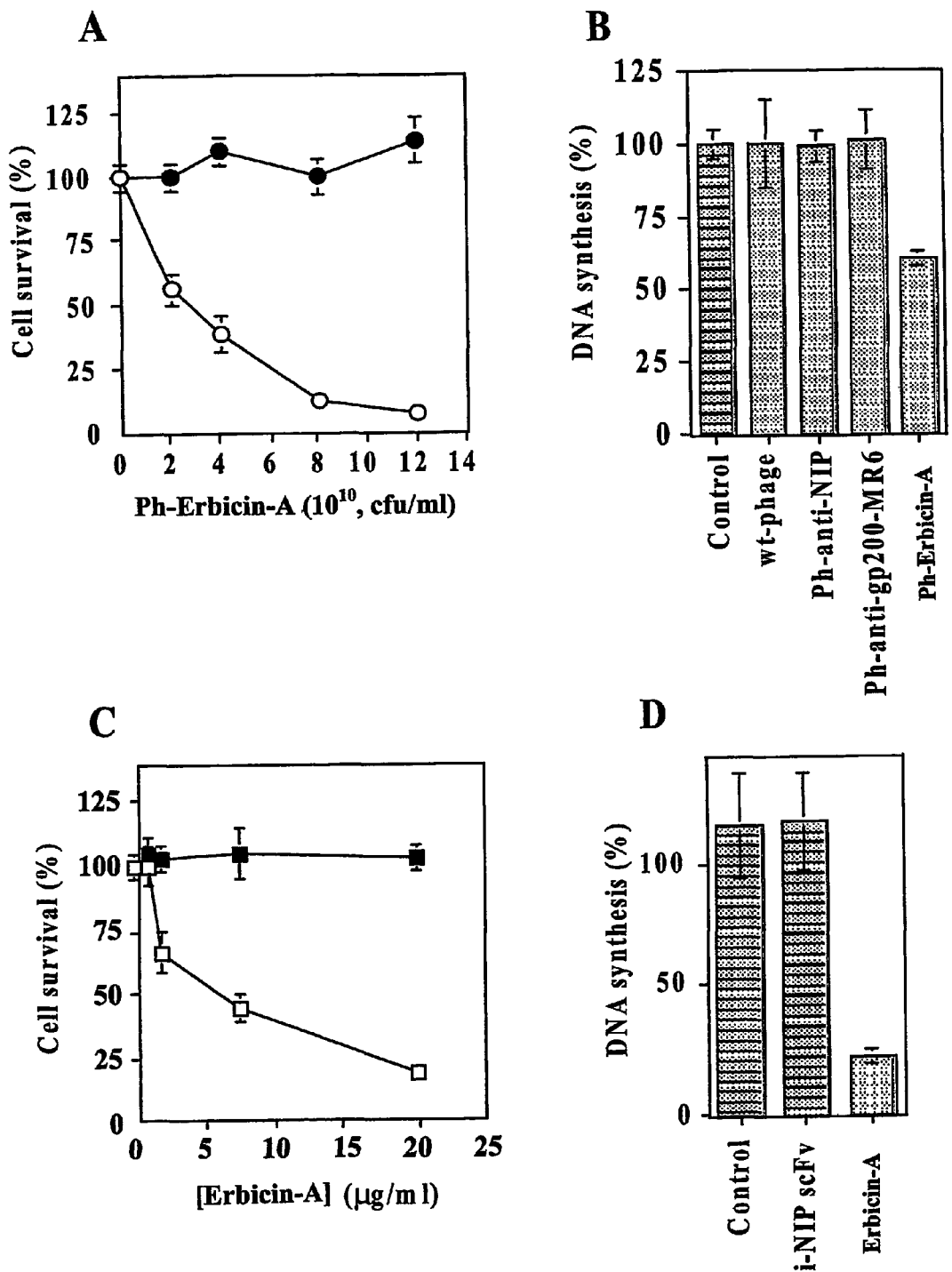
FIGS. 6A, 6B, 6C and 6D. Effects of Ph-Erbicin (FIG. 6A and FIG. 6B corresponding to panels A and B respectively) and Erbicin (FIG. 6C and FIG. 6D corresponding to panels C and D respectively) on the proliferation of SKBR3 (empty symbols in FIG. 6A and FIG. 6C corresponding to panels A and C respectively) and A431 (black symbols in FIG. 6A and FIG. 6C corresponding to panels A and C respectively) cell lines. In the dose-response curves, cell survival after 72 h is expressed as percentage of live cells with respect to untreated cells (about $3 \times 10^4$ cells).

Cells were plated in the presence or in the absence of increasing concentrations of Ph-Erbicin. After suitable time intervals the extent of cellular proliferation was measured by cell counts (FIG. 6A) or DNA synthesis (FIG. 6B). As a control, the experiment was repeated with phage preparations either lacking the Erbicin moiety, or displaying irrelevant scFv, such as anti-NIP or anti-gp200-MR6 (36). When tested on SKBR3 cells for 72 hours, Ph-Erbicin was found to severely inhibit their proliferation, with a dose-dependent cytotoxic effect (FIG. 6A). An $IC_{50}$ value, i.e. the concentration capable of inhibiting cellular proliferation by 50%, of $2.8 \times 10^{10}$ cfu/ml was calculated. No effects on cell proliferation were detected with control phages (FIG. 6B). Moreover, Ph-Erbicin had no effect on the proliferation of A431 cells (see FIG. 6A), which indicates the selective nature of the activity of this reagent.

When the anti-ErbB2 scFv was tested on SKBR3 cells in its soluble format, i.e. as Erbicin (see FIGS. 6C and D), it was found to retain its ability to severely inhibit cell proliferation, and to reduce viable cell numbers in a dose-dependent manner with an $IC_{50}$ value of 6.4 µg/ml (FIG. 6C). No effects were detected with the control anti-NIP scFv; likewise, Erbicin was found to be ineffective on A431 cells. In addition, the effect of Erbicin was also tested on the NIH 3T3 fibroblasts transfected with ErbB2. In this case, given the lower level of ErbB2 on the transfected cells compared to SKBR3 cells (see Table I), cells were starved prior to treatment, to enhance the immunoreagent (15 µg/ml) effect Under these conditions, less than 50% of cells survived, whereas the untransfected cells, tested in parallel, were unaffected by Erbicin (data not shown).

These results indicate that the novel human anti-ErbB2 scFv displays its ability to inhibit target cell proliferation in its soluble (Erbicin) as well as in its phage (Ph-Erbicin) format. To directly compare the potency of the cytotoxic activities of Erbicin and Ph-Erbicin on SKBR3 cells, the $IC_{50}$ value of $2.8 \times 10^{10}$ cfu/ml calculated for Ph-Erbicin (see above) was expressed also in terms of scFv concentration (1.3 ng/ml) in the phage preparation, assuming that one molecule of scFv is present per phage particle. By comparing this value to that obtained with Erbicin (6.4 µg/ml, see FIG. 6C), the scFv in the phage format appeared to be about 5000-fold more active as an antitumor agent than the soluble scFv.

Figure 7:
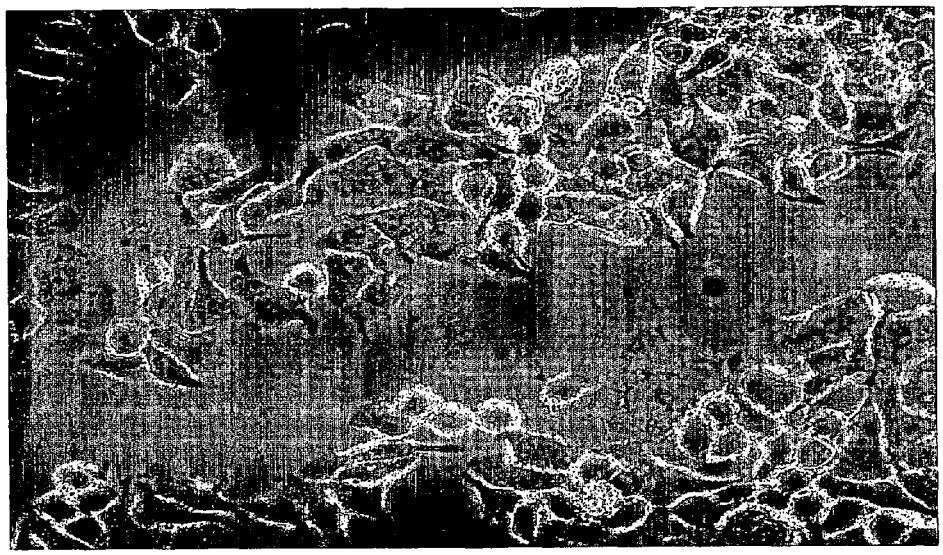
FIGS. 7A and 7B. The effects of Ph-Erbicin on SKBR3 cell morphology.
Figure 7:
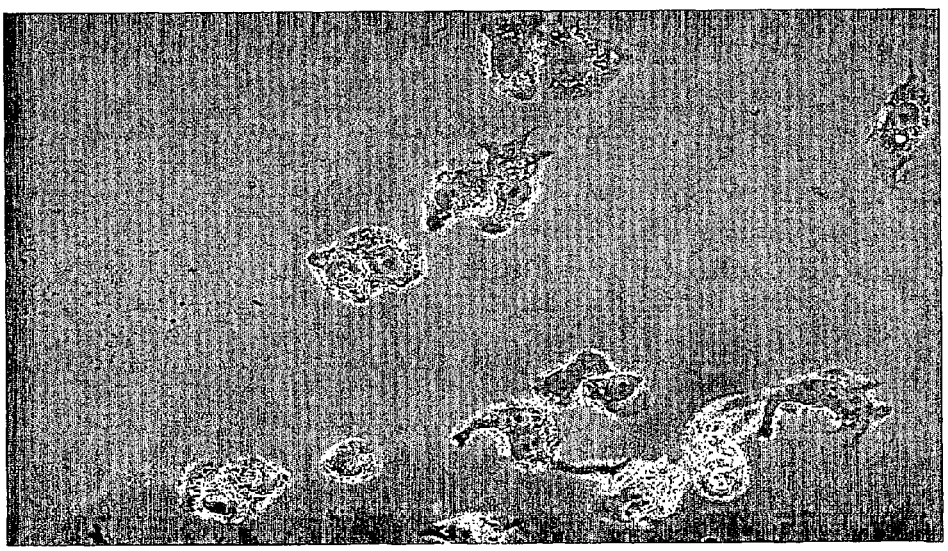

The ability of Ph-Erbicin to inhibit cell proliferation was also tested on other human tumor cells expressing high levels of ErbB2, such as MDA-MB453, BT-474, and SK-OV-3 cells, and on murine NIH 3T3 fibroblasts transfected with human ErbB2. All these ErbB2-positive cell lines were severely inhibited in their proliferation by Ph-Erbicin, whereas no anti-proliferative effect was detected on ErbB2-negative A431 cells and untransfected NIH 3T3 fibroblasts (see Table I). The $IC_{50}$ values obtained with these ErbB2-positive cells are in the range of $10^{11}$ cf/ml, i.e. one order of magnitude higher than the value determined for SKBR3 cells. It should also be noted that the effect of Ph-Erbicin on these four cell lines appeared to be cytostatic, rather than cytotoxic, as the number of surviving cells was never found to be lower than the number of plated cells. The higher sensitivity of SKBR3 cells to Ph-Erbicin is further supported by our observation that incubation of SKBR3 cells with Ph-Erbicin leads to a dramatic change in cell morphology and the appearance of cell debris; no such changes were seen with the other ErbB2-positive cell lines tested in this study (FIG. 7). These data suggest that the severe reduction of viable cells observed for SKBR3 treated with the Erbicin reagents is due to the induction of cell death.

To determine whether the mechanism of cell death occurs through induction of apoptosis, we used annexin V to measure the appearance of phosphatidylserine, a marker of apoptosis, on the outer leaflet of the plasma membrane of SKBR3 cells. Cells treated with either Ph-Erbicin or Erbicin were found to bind two-fold more FITC-conjugated annexin V than untreated cells or cells treated with a control anti-NIP scFv, either in its phage or its soluble format (Table II). This indicates that the cell death induced by Erbicin is that of apoptosis.

TABLE I

FACS analyses of Ph-Erbicin binding to a series of cell lines expressing different levels of ErbB2. Binding was measured from the average fluorescence intensity (MFI). The receptor expression levels were measured with the murine mAb MgR6 as specific anti-ErbB2 antibody. The effects of Ph-Erbicin on cell proliferation after 96 h of treatment, expressed as $IC_{50}$ values, are also tabulated.

| Cell line | Growth Inhibition ($IC_{50}$, cfu/ml) Ph-Erbicin | ErbB2 Binding (MFI)[a] Ph-Erbicin | MgR6 mAb |
|---|---|---|---|
| SKBR3 | $1,2 \times 10^{10}$ | 423 | 260 |
| MDA-MB453 | $1,4 \times 10^{11}$ | 260 | 160 |
| BT-474 | $2,5 \times 10^{11}$ | 100 | 145 |
| NIH 3T3 (ErbB2-trasf.) | $3,5 \times 10^{11}$ | 161 | 120 |
| SK-OV-3 | $4,0 \times 10^{11}$ | 90 | 92 |
| NIH 3T3 | —[b] | 30 | 10 |
| A431 | —[b] | 0 | 0 |

[a]The tabulated values were obtained by subtracting from the MFI values the basal fluorescence level determined with suitable control immunoreagents of the same isotype; these were the OKT3 mAb and the anti-NIP scFv, for data obtained with mAb MgR6 and Ph-Erbicin, respectively.
[b]No effects on cell proliferation were observed up to $4.0 \times 10^{11}$ cfu/ml of Ph-Erbicin.

TABLE II

Apoptosis of SKBR3 cells treated for 24 h with Ph-Erbicin, Erbicin or irrelevant immunoreagents

| | % apoptotic cells | MFI ratio[a] (treated cells/reference cells) |
|---|---|---|
| reference cells | 16 | 1 |
| Ph-anti-NIP | 16 | 1 |
| Ph-Erbicin | 30 | 2 |
| anti-NIP scFv | 19 | 1 |
| Erbicin | 34 | 2 |
| puromycin[b] | 35,6 | 1,7 |

[a]MFI is the intensity of average fluorescence measured by FACS after treatment of SKBR3 cells with Annexin V conjugated to FITC.
[b]The effect of puromycin on SKBR3 cells was evaluated after a 4 h incubation.

EXAMPLE 7

Cell Cultures.

The SKBR3 human breast tumor cell line and the A431 human epidermoid carcinoma cell line (kindly provided by Menarini Research, Pomezia, Italy) were cultured in RPMI 1640 (Gibco BRL, Life Technologies, Paisley, UK). The BT-474 and MDA-MB453 human breast tumor cell lines (a kind gift of H. C. Hurst, ICRF, London), the SK-OV-3 human ovarian cell line (a kind gift of I. McNeish, ICRF, London), and the NIH-3T3 murine fibroblasts (American Type Culture Collection, Rockville, Md., USA, code N. CRL-1658) were grown in DMEM (Gibco BRL). The NIH-3T3 fibroblast cell line transfected with human ErbB2, kindly provided by N. E. Hynes (Friederick Miescher Institute, Switzerland), was cultured in DMEM containing 1 mg/ml G418 (Gibco BRL). Media were supplemented with 10% fetal calf serum, 50 Units/ml pennicillin, and 50☐g/ml streptomycin (all from Gibco BRL).

EXAMPLE 8

Antibodies.

The following antibodies were used in the current study: murine anti-M13 mAb (Amersham Pharmacia Biotech, Little Chalfont, UK); murine nAb 9E10 directed against the myc tag protein (45); murine anti-His tag mAb (Qiagen, West Sussex, UK); murine anti-ErbB2 MgR6 mAb (gift from Menarini Research, Pomezia, Italy) (24); FITC-conjugated rabbit anti-mouse immunoglobulin antibody, and HRP-conjugated rabbit anti-mouse immunoglobulins (both from Dako, Cambridgeshire, UK); murine anti-phosphotyrosine mAb P-Tyr O?Y99) (Santa Cruz Biotechnology Inc., Santa Cruz, Calif.); anti-gp200-MR6 scFv was isolated as described in (36); murine anti-actin mAb (Sigma, St. Louis, Mo., USA). Anti-NIP (4-hydroxy-3-nitro-5-iodophenylacetyl) (27) and anti-thyroglobulin scFv were kindly provided by Dr. G. Winter.

EXAMPLE 9

Selections of scFv-phage on Live Cells.

ErbB2-positive cells were labeled as follows. The human breast tumor SKBR3 cell line, naturally expressing high levels of ErbB2, and the NIH-3T3 fibroblasts, transfected with human ErbB2, grown in 250 ml flasks (Becton Dickinson, Oxford, UK) to 70-80% confluency, were detached with the cell dissociation solution, purchased from Sigma and washed twice with PBS. Cells were then resuspended in 1 ml of pre-warmed PBS, containing 15 μM 5(6)-CFDA, SE (5-(and-6)-carboxyfluorescein diacetate, succinimidyl ester mixed isomers) (Molecular Probes, Eugene, Oreg.), and incubated for 30 min at 37° C. After three washes with cold PBS, cells were resuspended ($1 \times 10^6$ cells/nl), and the level of fluorescence analyzed by flow cytometry before each round of phage selection.

Phagemid particles were rescued with M13-K07 from the Griffin library, as previously described (18). For each round of panning, phages ($10^{13}$ cfu) were blocked with 5% milk powder (Marvel) in PBS for 15 min. The blocked phages were incubated for 16 hours at 4° C. with labeled "positive" cells ($1 \times 10^6$) in the presence of unlabeled "negative" cell ($9 \times 10^6$) by gently rotating, in a final volume of 5 ml containing 2% Marvel. Cells were then pelleted by centrifugation at 600×g for 5 min at 4° C., and washed twice in 50 ml of PBS. The "positive" labeled cells were sorted by FACS. To elute phages from "positive" cells, these were incubated with 0.5 ml PBS containing 50 mM citric acid (pH 2.5) for 5 min, and then neutralized with 0.4 ml of 1 M Tris-HCl pH 7.4. The recovered phages were amplified by infecting E. coli TG1 cells, to prepare phage for the next round of selection. Phage screening were carried out by cell ELISA assays as previously described (46).

EXAMPLE 10

Analysis of Clone Diversity.

To determine the number of individual selected clones, DNA fingerprinting analysis was performed with the restriction endonuclease BstNI or BsaJI (New England Biolabs, Hertfordshire, UK), as described (18). DNA encoding the variable region of positive clones was amplified by PCR from the pHEN2 plasmid, using as primers 5'-CAGTCTATGCG-GCCCCATTCA-3'SEQ ID N. 22 (complementary to the sequence located between gene II and the c-myc peptide tag) and 5'-ATGAAATACCT ATTGCCTACG-3' SEQ ID N. 23 (pel B leader sequence).

Reactions were performed with Taq DNA Polymerase (Promega, Southampton, UK) in a volume of 20 µl for 30 cycles under the following conditions: 30 seconds denaturing at 94° C., 30 seconds annealing at 55° C., and 1 min extension at 72° C. The amplified products, analyzed by electrophoresis on 1% agarose gel, were used for DNA fingerprinting and sequence analyses. The nucleotide sequences encoding scFv were determined using the ABI automated sequencer (Perlin Elmer, Warrington, UK) and were analyzed with the V-BASE sequence alignment program [Tomlinson I. M., Williams S. C., Corbeft S. J., Cox J. P. L. and Winter G. (1996). The V BASE Directory of Human Variable Gene Sequences. MRC Centre for protein Engineering, Hills Road, Cambridge, CB2 2QH, UK (http://www.mrc-cpe.cam.ac.uk/imt-doc/vbase-home-page.html)].

EXAMPLE 11

Cellular Lysis, Immunoprecipitation and Analysis by Western Blotting.

Cell lysates from SKBR3 were prepared by resuspending in 0.5 ml of lysis buffer (10 mM Tris-HCl, pH 7.4, 150 mM NaCl, 0.5% Nonidet P-40, containing protease inhibitors (Complete™ proteases inhibitor, Boehringer Mannheim, Germany) about $7.5 \times 10^6$ cells, previously detached with the dissociation solution (Sigma), and washed 3 times with PBS. After 20 min at 0° C., the extracts were clarified by centrifugation at 12,000 rpm for 10 min. ErbB2 immunoprecipitation was carried out by incubating the anti-ErbB2 MgR6 mAb with the cell lysates for 3 hours at 4° C. The immune complex was then collected by adsorption to protein G-Sepharose (Sigma) for 1 hour at 4° C. After four washes the proteins, released by boiling in loading buffer (47), were fractionated by 7.5% SDS gel-electrophoresis (SDS-PAGE) and electroblotted onto PVDF membranes (Millipore Corporation, Bedford, Mass. USA). The ErbB2 protein was detected using either anti-ErbB2 mAbs or scFv-phage preparations, as previously described (36).

EXAMPLE 12

Preparation of Monoclonal Phage Antibodies for Functional Assays.

scFv carrying phages were prepared from individual ampicillin-resistant colonies grown in 100 ml of 2×TY medium, purified by polyethylene glycol (PEG) precipitation (48) and washed with 20 ml of sterile water. After a further PEG precipitation step, phages were resuspended in PBS, centrifuged at 12,000 rpm for 15 min and stored at 4° C. until further use.

EXAMPLE 13

Soluble scFv Expression and Purification.

Cultures of E. coli SF110, previously infected with Ph-Erbicin or with anti-NIP scFv-phage, were grown at 37° C. in 2×TY media containing 100 µg/ml ampicillin and 1% glucose, until an absorbancy of 1 O.D. at 600 nm was reached. Cells were centrifuged at 6,000 rpm for 15 min and resuspended in glucose-free medium. The expression of soluble scFv was then induced by the addition of IPTG (Alexis, Nottingham, UK) to a final concentration of 1 mM in the cell culture, which was then grown at room temperature overnight. Cells were harvested by centrifugation at 6,000 rpm for 15 min, and a periplasmic extract was obtained by resuspending cells in ice-cold 50 mM Tris-HCl, pH 7.4, 1 mM EDTA, 20% sucrose. After an incubation of 1 hour on ice, the periplasmic extract, obtained by centrifugation at 12,000 rpm for 30 min at 4° C., was dialyzed in PBS. Alternatively, soluble periplasmic proteins were isolated using the B-PER buffer (Pierce, Rockford, Ill.) according to the manufacturer's recommendations.

Soluble scFv was purified on immobilized-metal affinity chromatography (IMAC), by incubating the periplasmic extract with Ni-NTA agarose (Qiagen, West Sussex, UK) overnight at 4° C. After extensive washes with PBS, containing 20 mM imidazole, the protein was eluted in 50 mM $NaH_2PO_4$, pH 8.0, containing 0.3 M NaCl and 250 mM imidazole. Further purification was achieved by gel-filtration on a Superdex 75 Hi-Load 10/30 column (FPLC) (Pharmacia Biotech, Upsala, Sweden) equilibrated in PBS containing 0.16 M NaCl, carried out at a flow rate of 0.3 ml/min. The purity of the final preparation was evaluated by SDS-PAGE. Protein bands were detected by Coomassie staining. Purified scFv, analyzed by Western blotting, was detected using either mAb 9E10 or anti-His tag mAb, followed by rabbit anti-mouse HRP-conjugated mAb, as previously described (36).

EXAMPLE 14

Determination of Tyrosine Phosphorylation.

SKBR3 cells were grown for 24 h in serum deprived RPMI medium, then treated with EGF (Collaborative Research Inc., Waltham, Mass.), or soluble Erbicin, at a concentration of 100 ng/ml and 12 µg/ml, respectively, in fresh, serum deprived medium. At the indicated times, cells were washed with PBS, harvested and lysed in the presence of 1 mM sodium orthovanadate. Western blotting analyses were performed with an anti-phosphotyrosine mAb. The signal intensity. of reactive bands was quantitated with a phosphorimager (GS-710, Bio-rad, Hercules, Calif.).

EXAMPLE 15

Internalization of Phage Antibodies and Native scFv.

Cells grown on coverslips to 60% confluency were incubated with phages ($10^{11}$ cfu/ml) or native scFv (20 µg/ml) for 2 or 16 hours at 37° C. Cells were then washed, fixed and permeabilized as described elsewhere (34). Intracellular phages or scFv were detected with either anti-M13 mAb or nAb 9E10, respectively, followed by FITC-conjugated rabbit anti-mouse immunoglobulin. Optical confocal sections were taken using a confocal microscope (Zeiss, Axiovert S100TV).

EXAMPLE 16

Flow Cytometry.

Approximately $1 \times 10^6$ cells were incubated with 100 µl of phage particles ($10^{12}$ cfu/ml), and mixed with 25 µl of 10% Marvel/PBS (36). Bound phage particles were detected using murine anti-M13 mAb, followed by FITC-conjugated rabbit anti-mouse immunoglobulin (Dako). The anti-ErbB2 mAb MgR6 was used at saturating concentrations in PBS containing 2% normal human serum, and detected using the FITC-conjugated rabbit anti-mouse immunoglobulin (Dako). Controls comprised cells incubated with the appropriate isotype-matched antibodies. For Annexin V immunofluorescence, cells were resuspended in binding buffer (10 mM HEPES, pH 7.4; 140 mM NaCl, 2.5 mM $CaCl_2$) and then stained with Annexin V-FITC and 7-amino-actinomycin D (7-AAD) according to the manufacturer's recommendations (PharMingen, Oxford, UK). Labeled cells were analyzed using the FACS Calibur flow cytometer (Becton Dickinson, Oxford, UK); the data were processed using CellQuest software (Becton Dickinson).

EXAMPLE 17

Cell Growth Inhibition Assays.

Cells were seeded in 96-well plates; SKBR3, BT-474 and MDA-MB453 cells at a density of $1.5 \times 10^4$/well in 150 µl; A431, NIH-3T3 and NIH-3T3 cells transfected with human ErbB2, at a density of $5 \times 10^3$/well. Phages ($10^{10}$-$10^{11}$ cfu/ml) or soluble purified scFv (1-20 µg/ml) were added, and at suitable time intervals surviving cells were counted. Cell counts were determined in triplicate by the trypan blue exclusion test. In parallel experiments cells were pulsed for 8 h with [$^3$H]thymidine (Amersham-Pharmacia Biotech, Little Chalfont, UK) prior to harvest, and the incorporated radioactivity was measured.

To test apoptotic death, SKBR3 cells were seeded in 6-well plates at a density of $3 \times 10^5$/well, in the absence or in the presence of Ph-Erbicin ($10^{11}$ cfu/ml) or Erbicin (15 µg/ml). The irrelevant anti-NIP scFv was tested in its phage and soluble format as a control. After 24 hours, cells were harvested, washed in PBS, and treated with Annexin V as described above. The apoptotic inducer puromycin (10 µml) was used as a positive control.

EXAMPLE 18

Preparation of hERB-RNase

Figure 8:
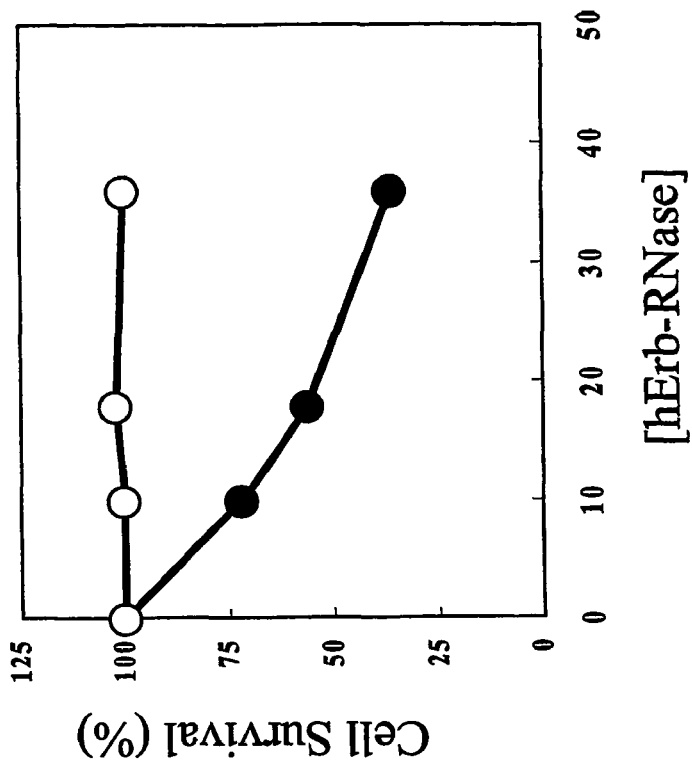
FIGS. 8A and 8B. Binding of hERB-RNase to ErbB2-positive and -negative cells and its effects on cell survival.
Figure 8:
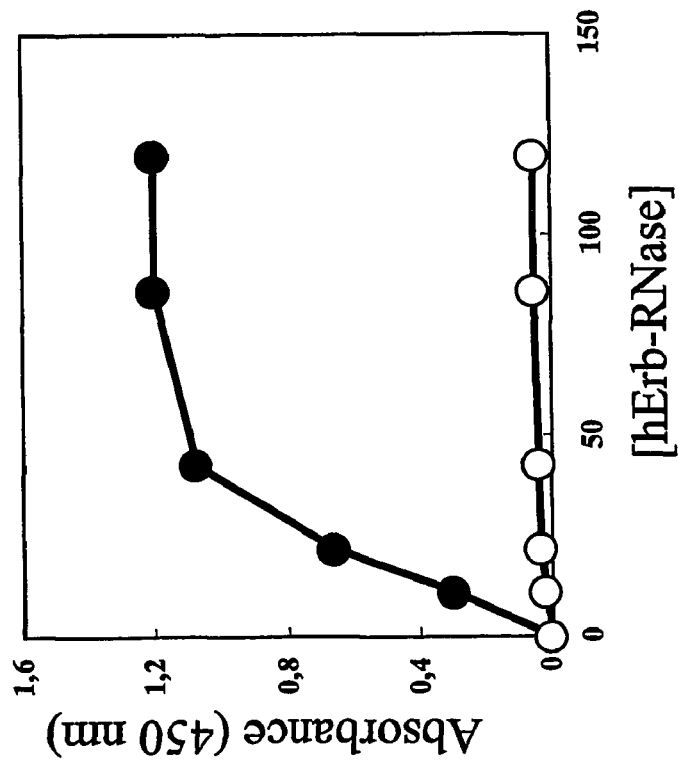

The fully human immunoRNase hERB-RNase was prepared as follows: The cDNA encoding human pancreas RNase, containing a spacer sequence at the 5' terminus and a Not I recognition site at both termini, was cloned in the expression vector pHEN2 (27) downstream to the sequence encoding Erbicin, previously inserted in NcoI/NotI sites. SF110 E. coli cells were transformed with the recombinant vector and induced with IPTG. hERB-RNase was isolated from a bacterial peryplasmic extract by "immobilized-metal affinity chromatography" (IMAC) on a Talon resin, followed by an affinity chromatography on a uridine-2'-5',3'-5'-diphosphate-agarose resin. The recombinant protein was analyzed by Blue Coomassie staining and Western blots performed with an anti human pancreas RNase antibody. The ribonucleolytic activity was tested by a zymogram developed with yeast RNA as an RNase substrate. The binding specificity was tested by Elisa assays on SKBR3 and A431 cells. The effects of hERB-RNase on cell proliferation were tested as described in Example 6. After a 72 h incubation with increasing concentrations of hERB-RNase, the proliferation of SKBR3 cells was strongly inhibited, with an IC50 value of about 20nM (see FIG. 8). When instead A431 cells were tested as non-target cells, no effects on their proliferation were observed. These results indicate that the fuilly human imnnunoRNase hERB-RNase is able to discriminate between target and non-target cells, and to specifically induce the death of target cells.

BIBLIOGRAPHY

1. Yamamoto, T. et al., *Nature* 319, 230-234 (1986).
2. King, C. R. et al., *Science* 229, 974 976 (1985).
3. Slamon, D. J. et al., *Science* 244, 707-712 (1989).
4. Tagliabue, E. et al., *Int. J. Cancer* 47, 933-937 (1991).
5. Fukushige, S. et al., *Mol. Cell. Biol.* 6, 955-958 (1986).
6. Semba, K et al., *Proc. Natl. Acad. Sci. USA* 82, 6497-6501 (1985).
7. Press, M. F. et al., *Oncogene* 5, 953-962 (1990).
8. Graus-Porta, D. et al., *Embo J.* 16, 1647-1655 (1997).
9. Hudziak, R. M. et al., *Proc. Natl. Acad. Sci. USA* 85, 5102-5106 (1988).
10. Hudziak, R. M. et al., *Mol. Cell. Biol.* 9, 1165-1172 (1989).
11. Harwerth, I. M. et al., *J. Biol. Chem.* 267, 15160-15167 (1992).
12. Kita, Y. et al., *Biochem. Biophys. Res. Commun.* 226, 59-69 (1996).
13. Harwerth, I. M. et al., *Br. J. Cancer* 68, 1140-1145 (1993).
14. Park, J. W. et al., in *Genes, Oncogenes and Hormones: Advances in Cellular and Molecular Biology of Breast Cancer* (eds Dickinson, R. B. & Lippman, M. E.) 193-211, Kluver, Boston, 1992).
15. Carter, P. et al., *Proc. Nati. Acad. Sci. USA* 89, 4285-4289 (1992).
16. Holliger, P. et al., *Nat. Biotechnol* 16, 1015-1016 (1998).
17. Carter, P. et al., *Breast Disease* 11, 103-111 (2000).
18. Marks, J. D. et al., *J. Mol. Biol.* 222, 581-597 (1991).
19. Griffiths, A. D. et al., *EMBO J.* 13, 3245-3260 (1994).
20. Schier, R. et al., *Immunotechnology* 1, 73-81 (1995).
21. Sheets, M. D. et al., *Proc. Natl. Acad. Sci. USA* 95, 6157-6162 (1998).
22. Poul, M. A. et al., *J. Mol. Biol.* 301, 1149-1161 (2000).
23. Olayioye, M. A. et al., *Mol. Cell. Biol.* 18, 5042-5051 (1998).
24. Centis, F. et al., *Hybridoma* 11, 267-276 (1992).
25. Orlandi, R. et al., *Biol. Chem.* 378, 1387-1392 (1997).
26. Parente, D. et al., *J. Biochem.* 239, 272-280 (1996).
27. Nissim, A. et al., *EMBO J.* 13, 692-698 (1994).
28. Coussens, L. et al., *Science* 230, 1132-1139 (1985).
29. Hynes, N. E. et al., *J. Cell. Biochem.* 39, 167-173 (1989).
30. Haigler, H. et al., *Proc. Nati. Acad. Sci. USA* 75, 3317-3321 (1978).

31. Fabricant, R. N. et al., *Proc. Nati. Acad. Sci. USA* 74, 565-569 (1977).
32. Meerman, H. J. et al., *Biotechnology (NY)* 12, 1107-1110 (1994).
33. Kipriyanov, S. M. et al., *J. Immunol. Methods* 196, 51-62 (1996).
34. Becerril, B. et al., *Biochem. Biophys. Res. Commun.* 255, 386-393 (1999).
35. Sarup, J. C. et al., *Growth Regul.* 1, 72-82 (1991).
36. Palmer, D. B. et al., *Immunology* 96, 236-245 (1999).
37. de Kruif, J. et al., *Immunol. Today* 17, 453-455 (1996).
38. Palmer, D. B. et al., *Immunology* 91, 473.-478 (1997).
39. de Kruif, J. et al., *Proc. Natl. Acad. Sci. USA* 92, 3938-3942 (1995).
40. Huls, G. A. et al., *Nat. Biotechnol.* 17, 276-281 (1999).
41. Daly, J. M. et. al, *Cancer Res.* 57, 3804-3811 (1997).
42. Srinivas, U. et al., *Cancer Immunol. Immunother.* 36, 397-402 (1993).
43. Marks, J. D. et al., *J. Biol. Chem.* 267, 16007-16010 (1992).
44. de Kruif, J. et al., *J. Biol. Chem.* 271, 7630-7634 (1996).
45. Evan, G. I. et al., *Mol. Cell. Biol.* 5, 3610-3616 (1985).
46. Ridgway, J. B. et al., *Cancer Res.* 59, 2718-2723 (1999).
47. Laemmli, U. *Nature* 227, 680-685 (1970).
48. Sambrook, J. et al., T. *Molecular cloning: a laboratory manual*, (Cold Spring Harbor Laboratory Press, Cold Spring Arbor, N.Y., 1990).
49. Mariuzza, R. A et al., *Annual Rev. Biophys. Chem.* Vol. 16, 139-159 (1978).
50. Powers, D. B. et al., *J. Immunol. Methods* 251, 123-135 (2001).

The invention claimed is:

1. An isolated recombinant antibody comprising a sequence selected from the group consisting of:
   (a) SEQ ID NO:2 (VH region) and SEQ ID NO:12 (VL region) covalently linked by a peptide linker, wherein the antibody inhibits growth of cells expressing ErB2 receptor, and
   (b) SEQ ID NO:20, wherein the antibody inhibits growth of cells expressing ErB2 receptor.

2. A recombinant antibody according to claim 1 comprising Complementarity Determining Regions (CDR) having amino acid sequences corresponding to SEQ ID NO:4, 6, and 8 and amino acid sequences corresponding to SEQ ID NO:14, 16 and 18.

3. A recombinant antibody according to claim 1 able to inhibit the tyrosine kinase activity of the receptor.

4. A recombinant antibody according to claim 1 characterized in that it inhibits the growth of SKBR3 cells by at least 65%.

5. An isolated human antibody which binds to ErbB2, said antibody comprising:
   a heavy chain variable region comprising CDR-1 as set forth in SEQ ID NO: 4, CDR-2 as set forth in SEQ ID NO: 6 and CDR-3 as set forth in SEQ ID NO: 8; and
   a light chain variable region comprising CDR-1 as set forth in SEQ ID NO: 14, CDR-2 as set forth in SEQ ID NO: 16, and CDR3 as set forth in SEQ ID NO: 18.

6. The antibody of claim 5, wherein said antibody is a single chain antibody.

7. The antibody of claim 5, comprising the amino acid sequence of SEQ ID NO:2 (VH region) and the amino acid sequence of SEQ ID NO:12 (VL region).

8. The antibody of claim 7, wherein the VH region of SEQ ID NO:2 and the VL region of SEQ ID NO:12 are covalently linked by a peptide linker.

9. The antibody of claim 5 comprising the amino acid sequence of SEQ ID NO: 20.

10. The antibody of claim 5, capable of inhibiting the growth of SKBR3 cells by at least 65%.

11. A fusion protein characterized in that it comprises at least one of the amino acid sequences according to claim 1.

12. A fusion protein according to claim 11 wherein said amino acid sequences are fused to constant regions from human antibodies, or to toxins or to molecules with cytotoxic effect.

13. A composition comprising an isolated antibody which binds to ErbB2, said antibody comprising:
   a human heavy chain variable region comprising CDR-1 as set forth in SEQ ID NO: 4, CDR-2 as set forth in SEQ ID NO: 6, and CDR-3 as set forth in SEQ ID NO: 8; and
   a human light chain variable region comprising CDR-1 as set forth in SEQ ID NO: 14, CDR-2 as set forth in SEQ ID NO: 16, and CDR3 as set forth in SEQ ID NO: 18.

14. The composition of claim 13, further comprising a pharmaceutically suitable diluent.

15. The composition of claim 13, further comprising a pharmaceutically suitable excipient.

16. The composition of claim 13, further comprising a pharmaceutically suitable adjuvant.

17. The composition of claim 13, further comprising a protein fused to said antibody.

18. The composition of claim 13, wherein said human heavy chain variable region is fused to a constant region from human immunoglobulin G1.

19. The composition of claim 18, wherein said constant region consists of a CH2 domain, a CH3 domain, and a hinge region from human immunoglobulin G1.

20. The composition of claim 13, wherein said composition comprises a fusion protein comprising said antibody and a molecule having cytotoxic effect.

21. The composition of claim 13, wherein said composition comprises a fusion protein comprising said antibody and a toxin.

22. The composition of claim 13, wherein said composition comprises a fusion protein comprising said antibody and a protease.

23. The composition of claim 13, wherein said composition comprises a fusion protein comprising said antibody and a human ribonuclease.

24. The composition of claim 23, wherein the human ribonuclease is human pancreatic ribonuclease.

25. The composition of claim 17, wherein said composition comprises a fusion protein which specifically binds cell-surface ErbB2 receptor on ErbB2-positive tumor cells and inhibits proliferation of the tumor cells.

26. The composition of claim 13, wherein said composition comprises the antibody coupled to the surface of a phage.

27. A composition comprising the antibody of claim 5 and a pharmaceutically suitable diluent.

28. A composition comprising the antibody of claim 9 and a pharmaceutically suitable diluent.

29. The composition of claim 13, wherein said antibody is a single chain antibody.

30. A method to inhibit the proliferation of cells overexpressing the Erb-B2 receptor comprising administering to a subject in need of the therapy a therapeutically effective amount of the antibody according to claim 1 or 5 or a composition of claim 13.

31. A method according to claim 30 wherein said Erb-B2 overexpressing cells are selected from the group consisting of: mammary carcinomas, ovarian carcinomas, colon carcinomas, lung carcinomas, salivary glands tumor, and gastric tumor.

32. A method of stimulating anti-tumor activity comprising administering to a subject in need thereof the composition according to claim 13.

33. The method of claim 32, wherein the tumor is selected from the group consisting of: mammary carcinoma, ovarian carcinoma, colon carcinoma, lung carcinoma, salivary gland tumor, and gastric tumor.

34. A method of stimulating anti-tumor activity comprising administering to a subject in need thereof the composition according to claim 17.

35. The method of claim 34, wherein the tumor is selected from the group consisting of: mammary carcinoma, ovarian carcinoma, colon carcinoma, lung carcinoma, salivary gland tumor, and gastric tumor.

36. A method of stimulating anti-tumor activity comprising administering to a subject in need thereof the composition according to claim 23.

37. The method of claim 36, wherein the tumor is selected from the group consisting of: mammary carcinoma, ovarian carcinoma, colon carcinoma, lung carcinoma, salivary gland tumor, and gastric tumor.

38. A method of stimulating anti-tumor activity comprising administering to a subject in need thereof the composition according to claim 26.

39. The method of claim 38, wherein the tumor is selected from the group consisting of: mammary carcinoma, ovarian carcinoma, colon carcinoma, lung carcinoma, salivary gland tumor, and gastric tumor.

40. A method of stimulating anti-tumor activity comprising administering to a subject in need thereof the composition according to claim 29.

41. A method of claim 40, wherein the tumor is selected from the group consisting of: mammary carcinoma, ovarian carcinoma, colon carcinoma, lung carcinoma, salivary gland tumor and gastric tumor.

42. A method for the preparation of a recombinant human anti-ErbB2 antibody able to inhibit growth of cells expressing the ErbB2 receptor and comprising an amino acid sequence selected from the group consisting of:
 (a) SEQ ID NO:2 (VH region) and SEQ ID NO:12 (VL region), and
 (b) SEQ ID NO: 20,
the method comprising expressing the amino acid sequence from a vector comprising a sequence selected from the group consisting of:
 (i) SEQ ID NO:1 and SEQ ID NO:11, and
 (ii) SEQ ID NO:19.

43. A method according to claim 42 comprising the following steps: infection of *E. coli* cultures with a phagemid vector comprising a nucleotide sequence selected from the group consisting of:
 (a) SEQ ID NO: 1 and SEQ ID NO: 11, and
 (b) SEQ ID NO: 19,
growth of the *E.coli* in culture medium containing antibiotics up to an absorbancy value of 1 O.D.;
induction with IPTG;
expression;
preparation of the periplasmic extract;
isolation of a recombinant human single chain anti-ErbB2 antibody able to inhibit growth of cells expressing the ErbB2 receptor comprising an amino acid sequence selected from the groups consisting of:
 (i) SEQ ID NO: 2 (VH region) and SEQ ID NO: 12 (VL region), and
 (ii) SEQ ID NO: 20 from the periplasmic extract by affinity chromatography; and
purification by gel filtration.

44. A method for the preparation of the fusion protein according to claim 12 comprising the following steps: (i) isolation of a nucleotide sequence encoding a single chain human anti-ErbB2 antibody able to inhibit growth of cells expressing the ErbB2 receptor and comprising an amino acid sequence selected from the group consisting of: (a) SEQ ID NO: 2 (VH region) and SEQ ID NO: 12 (VL region), and (b) SEQ ID NO: 20; (ii) fusion of said DNA sequence to a cDNA encoding the constant regions (CH2 and CH3) and the hinge peptide from human heavy chains of immunoglobulin G1; (iii) expression of the resulting fusion cDNA in eukaryotic cells.

\* \* \* \* \*

UNITED STATES PATENT AND TRADEMARK OFFICE
CERTIFICATE OF CORRECTION

PATENT NO.       : 7,585,952 B2                                    Page 1 of 1
APPLICATION NO.  : 10/483803
DATED            : September 8, 2009
INVENTOR(S)      : Giuseppe D'Alessio et al.

It is certified that error appears in the above-identified patent and that said Letters Patent is hereby corrected as shown below:

Title Page;
On the first (front) page of the patent, the assignee's name is misspelled, and the correct spelling is:

(73)    Assignee: Biotecnol S.A., Oeiras

Signed and Sealed this

Fifth Day of January, 2010

David J. Kappos
*Director of the United States Patent and Trademark Office*